(12) United States Patent
Zagar et al.

(10) Patent No.: US 8,754,010 B2
(45) Date of Patent: Jun. 17, 2014

(54) HERBICIDAL MIXTURES

(75) Inventors: Cyrill Zagar, Mannheim (DE); Adam F. Burnhams, Cary, NC (US); Peter Dombo, Wiesbaden (DE); Andreas Landes, Roemerberg-Heiligenstein (DE); Bernd Sievernich, Hassloch (DE); Herve R. Vantieghem, Stutensee-Staffort (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 13/565,211

(22) Filed: Aug. 2, 2012

(65) Prior Publication Data

US 2012/0302441 A1 Nov. 29, 2012

Related U.S. Application Data

(63) Continuation of application No. 10/549,268, filed as application No. PCT/EP2004/002632 on Mar. 12, 2004, now abandoned.

(60) Provisional application No. 60/453,973, filed on Mar. 13, 2003.

(51) Int. Cl.
   A01N 43/40 (2006.01)
   A01N 43/64 (2006.01)
   A01N 43/58 (2006.01)
   A01N 43/36 (2006.01)

(52) U.S. Cl.
   USPC .......... 504/130; 504/133; 504/134; 504/137; 504/138

(58) Field of Classification Search
   CPC ........ A01N 43/40; A01N 43/54; A01N 43/66
   See application file for complete search history.

(56) References Cited

U.S. PATENT DOCUMENTS

| | | | |
|---|---|---|---|
| 6,030,924 A | 2/2000 | Mayer et al. | |
| 6,683,027 B2 * | 1/2004 | Baltruschat et al. | 504/128 |
| 7,138,360 B2 | 11/2006 | Jager et al. | |
| 2003/0060367 A1 | 3/2003 | Bieringer et al. | |
| 2003/0181333 A1 | 9/2003 | Hacker et al. | |
| 2003/0186816 A1 | 10/2003 | Hacker et al. | |

FOREIGN PATENT DOCUMENTS

| | | |
|---|---|---|
| DE | 10245222 A1 | 4/2003 |
| JP | 07000069 * | 1/1995 |
| WO | 9407368 A1 | 4/1994 |
| WO | 0126466 A2 | 4/2001 |
| WO | 03024227 A1 | 3/2003 |
| WO | 2004017737 A | 3/2004 |

OTHER PUBLICATIONS

RD-45104, Nov. 2011, RD, Anon.*
451014, RD, Nov. 10, 2001, Anon.

* cited by examiner

*Primary Examiner* — Alton Pryor
(74) *Attorney, Agent, or Firm* — Rothwell, Figg, Ernst & Manbeck, P.C.

(57) ABSTRACT

A synergistic herbicidal mixture comprising
A) picolinafen;
   or one of its environmentally compatible salts;
and
B) a synergistically effective amount of at least a sulfonylurea of formula II

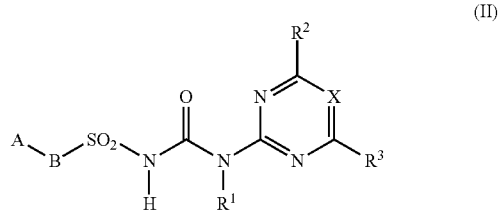

wherein the variables A, B, X and $R^1$ to $R^3$ have the meanings given in the specification;
and, if desired,
C) at least a safener.
Compositions comprising these mixtures, processes for the preparation of these compositions and their use for controlling undesired plants.

11 Claims, No Drawings

HERBICIDAL MIXTURES

This application is a continuation of U.S. Ser. No. 10/549,268 filed Aug. 14, 2006, which is a 35 U.S.C. 371 National Phase Entry Application from PCT/EP02/02632, filed Mar. 12, 2004, which is a non-provisional of U.S. Ser. No. 60/453,973 filed Mar. 13, 2003.

The present invention relates to a synergistic herbicidal mixture comprising

A) picolinafen (I)

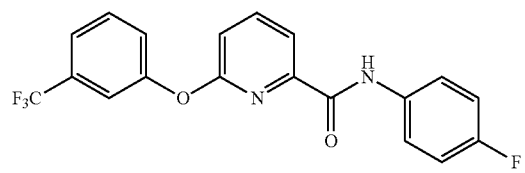

or one of its environmentally compatible salts;

and

B) a synergistically effective amount of at least a sulfonylurea of formula II

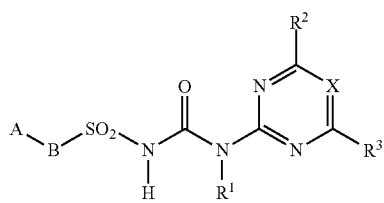

wherein

A is A1, A2, A3, A4 or A5

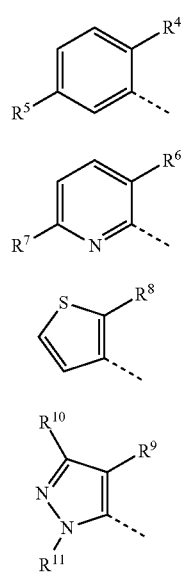

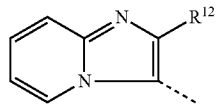

wherein $R^4$ is halogen, $C_1$-$C_4$-haloalkyl, $C_1$-$C_4$-alkoxy, $C_1$-$C_4$-haloalkoxy, $C_1$-$C_2$-alkoxy-$C_1$-$C_4$-alkoxy, cyclopropylcarbonyl, di($C_1$-$C_4$-alkyl)aminocarbonyl or hydroxycarbonyl;

$R^5$ is hydrogen, halogen or $C_1$-$C_4$-alkylsulfonylamino-$C_1$-$C_4$-alkyl;

$R^6$ is hydroxycarbonyl or $C_1$-$C_4$-alkylsulfonyl;

$R^7$ is hydrogen or $C_1$-$C_4$-haloalkyl;

$R^8$ is hydroxycarbonyl;

$R^9$ is 2-methyl-tetrazol-5-yl or hydroxycarbonyl;

$R^{10}$ is hydrogen or halogen;

$R^{11}$ is $C_1$-$C_4$-alkyl;

$R^{12}$ is halogen or $C_1$-$C_4$-alkylsulfonyl;

B is —O—, —NH—, —$CH_2$— or a bond;

$R^1$ is hydrogen or $C_1$-$C_4$-alkyl;

$R^2$ is halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylamino or di($C_1$-$C_4$-alkyl)-amino;

$R^3$ is $C_1$-$C_4$-alkyl, $C_1$-$C_4$-haloalkoxy or $C_1$-$C_4$-alkoxy;

X is CH or N;

or one of its environmentally compatible salts or esters;

and, if desired,

C) at least a safener selected from the group of dichlormid, benoxacor, LAB 145 138, MG-191, furilazole, cyometrinil, oxabetrinil, fluxofenim, flurazole, naphthalic acid anhydride, fenclorim, fenchlorazole-ethyl, mefenpyr, isoxadifen, cloquintocet, 1-ethyl-4-hydroxy-3(1H-tetrazol-5-yl)-1H-quinolin-2-one, 4-carboxymethyl-chroman-4-carboxylic acid, N-(2-methoxybenzyl)-4-(3-methylureido)-benzene-sulfonamide and (3-oxo-isothiochroman-4-ylidenmethoxy)acetic acid methyl ester;

or one of its environmentally compatible salts, esters or amides.

The invention furthermore relates to herbicidal compositions comprising a herbicidally active amount of a synergistic herbicidal mixture as defined above and at least one liquid and/or solid carrier and, if desired, at least one surfactant.

Moreover, the invention relates to processes for the preparation of these compositions and to a method of controlling undesirable vegetation.

WO 94/07368 and WO 01/26466 disclose mixtures of picolinafen with special further herbicides. However, in crop protection products, it is always desirable to increase the specific activity of an active ingredient and the reliability of action. It is an object of the present invention to increase the activity and/or selectivity of picolinafen against undesirable harmful plants.

We have found that this object is achieved by the mixtures defined at the outset. We have furthermore found herbicidal compositions which comprise these mixtures, processes for their preparation, and methods of controlling undesirable vegetation. In the last-mentioned cases, it is irrelevant whether the herbicidally active compounds of group A), B) and, if desired, C) are formulated and applied jointly or separately and in which sequence they are applied in the case of separate application.

The mixtures according to the invention show a synergistic effect; the compatibility of the herbicidally active compounds of group A), B) and, if desired C) for certain crop plants is generally retained.

The compounds of component A) may exist, or be used, in the form of their environmentally compatible salts; the compounds of component B) may exist, or be used, in the form of their environmentally compatible salts or esters and, if desired the compounds of component C) may exist, or be used, in the form of their environmentally compatible salts, esters and amides.

Suitable salts, esters and amides are, in general, those ones which do not adversely affect the herbicidal action or safening of the active ingredients.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four atoms to be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropyl-ammonium, tetramethylammonium, tetrabutylammonium, 2-(2-hydroxyeth-1-oxy)eth-1-yl ammonium, di(2-hydroxyeth-1-yl)-ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of suitable acid addition salts are mainly chloride, bromide, fluoride, hydrogen sulfate, sulfate, dihydrogen phos-phate, hydrogen phosphate, nitrate, hydrogen carbonate, carbo-nate, hexafluorosilicate, hexafluorophosphate, benzoate and the anions of $C_1$-$C_4$-alkanoyl acids, preferably formate, acetate, propionate and butyrate.

Suitable esters are alkly-, alkoxyalkyl-, allyl-, propargyl- and oxetan-3-yl-esters, preferably $C_1$-$C_{10}$-esters, for example methyl-, ethyl-, propyl-, isopropyl-, butyl-, isobutyl-, pentyl-, mexyl-(1-ethylhexyl) or isooctyl-(2-ethylhexyl)ester, $C_1$-$C_4$-alkoxy-ethyl-esters, for example methoxyethyl-, ethoxyethyl- or butoxyethyl-ester, allylesters, propar-gylesters and oxetan-3-ylesters.

Suitable amides are "amide" itself, alkyl- and dialkyl-amides as well as anilides, preferably $C_1$-$C_4$-alkylamides, for example methyl- or ethyl amide, di($C_1$-$C_4$-alkyl)amides, for example dimethyl- or diethyl amide, or anilides, preferably anilide itself or 2-chloroanilide.

The organic moieties mentioned for the substituents $R^1$ to $R^{12}$ are collective terms for individual enumerations of the individual group members. All hydrocarbon chains, i.e. all alkyl, haloalkyl, alkoxy, haloalkoxy, alkylsulfonyl, alkylamino, dialkylamino, dialkylminocarbonyl and alkylsulfonylaminoalkyl moities can be straight-chain or branched. Unless indicated otherwise, halogenated substituents preferably carry one to five identical or different halogen atoms. The term "halogen" represents in each case fluorine, chlorine, bromine or iodine.

Examples of other meanings are:

$C_1$-$C_2$-alkyl: methyl and ethyl;

$C_1$-$C_3$-alkyl: $C_1$-$C_2$-alkyl as mentioned above, and propyl and 1-methylethyl;

$C_1$-$C_4$-alkyl: $C_1$-$C_s$-alkyl as mentioned above, and butyl, 1-methylpropyl, 2-methylpropyl and 1,1-dimethylethyl;

$C_1$-$C_2$-haloalkyl: a $C_1$-$C_2$-alkyl radical as mentioned above which is partially or fully substituted by fluorine, chlorine, bromine and/or iodine, for example chloromethyl, dichloro-methyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromo-ethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$-$C_3$-haloalkyl: $C_1$-$C_2$-haloalkyl as mentioned above, and 2-fluoropropyl, 3-fluoropropyl, 2,2-difluoropropyl, 2,3-di-fluoropropyl, 2-chloropropyl, 3-chloropropyl, 2,3-dichloro-propyl, 2-bromopropyl, 3-bromopropyl, 3,3,3-trifluoropropyl, 3,3,3-trichloropropyl, 2,2,3,3,3-pentafluoropropyl, hepta-fluoropropyl, 1-(fluoromethyl)-2-fluoroethyl, 1-(chloromethyl)-2-chloroethyl and 1-(bromomethyl)-2-bromoethyl;

$C_1$-$C_4$-haloalkyl: $C_1$-$C_3$-haloalkyl as mentioned above, 4-fluoro-butyl, 4-chlorobutyl, 4-bromobutyl and nonafluorobutyl;

$C_1$-$C_2$-alkoxy and the alkoxy moieties of $C_1$-$C_2$-alkoxy-$C_1$-$C_2$-alkoxy and $C_1$-$C_2$-alkoxy-$C_1$-$C_4$-alkoxy: methoxy and ethoxy;

$C_1$-$C_3$-alkoxy and the alkoxy moieties of $C_1$-$C_2$-alkoxy-$C_1$-$C_3$-alkoxy: $C_1$-$C_2$-alkoxy as mentioned above, and propoxy and 1-ethylethoxy;

$C_1$-$C_4$-alkoxy and the alkoxy moieties of $C_1$-$C_2$-alkoxy-$C_1$-$C_4$-alkoxy: $C_1$-$C_3$-alkoxy as mentioned above, and butoxy, 1-methylpropoxy, 2-methylpropoxy and 1,1-dimethylethoxy;

$C_1$-$C_2$-haloalkoxy: a $C_1$-$C_2$-alkoxy radical as mentioned above which is partially or fully substituted by fluorine, chlorine, bromine and/or iodine, for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy;

$C_1$-$C_4$-haloalkoxy: $C_1$-$C_2$-haloalkoxy as mentioned above, and 2-fluoropropoxy, 3-fluoropropoxy, 2-chloropropoxy, 3-chloro-propoxy, 2-bromopropoxy, 3-bromopropoxy, 2,2-difluoro-propoxy, 2,3-difluoropropoxy, 2,3-dichloropropoxy, 3,3,3-trifluoropropoxy, 3,3,3-trichloropropoxy, 2,2,3,3,3-penta-fluoropropoxy, heptafluoropropoxy, 1-(fluoromethyl)-2-fluoro-ethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_2$-alkylsulfonyl ($C_1$-$C_2$-alkyl-S($=$O)$_2$—): methylsulfonyl and ethylsulfonyl;

$C_1$-$C_3$-alkylsulfonyl: $C_1$-$C_2$-alkylsulfonyl as mentioned above, and propylsulfonyl and 1-methylethylsulfonyl;

$C_1$-$C_4$-alkylsulfonyl: $C_1$-$C_3$-alkylsulfonyl as mentioned above, and butylsulfonyl, 1-methylpropylsulfonyl, 2-methylpropyl-sulfonyl and 1,1-dimethylethylsulfonyl;

$C_1$-$C_2$-alkylamino: methylamino and ethylamino;

$C_1$-$C_4$-alkylamino: $C_1$-$C_2$-alkylamino as mentioned above, and propylamino, 1-methylethylamino, butylamino, 1-methylpropyl-amino, 2-methylpropylamino and 1,1-dimethylethylamino;

di($C_1$-$C_2$-alkyl)amino: for example N,N-dimethylamino, N-ethyl-N-methyl-amino, and N,N-diethylamino;

di($C_1$-$C_4$-alkyl)amino: di($C_1$-$C_2$-alkyl)amino as mentioned above, and N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propyl-amino, N-(1,1-dimethylethyl)-N-propyl-amino, N-butyl-N-(1-methylethyl)amino, N-(1-methyl-ethyl)-N-(1-methylpropyl)-amino, N-(1-methylethyl)-N-(2-methylpropyl)amino, N-(1,1-dimethylethyl)-N-(1-methylethyl)-amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_2$-alkyl)aminocarbonyl: for example N,N-dimethylamino-carbonyl, N-ethyl-N-methylaminocarbonyl and N,N-diethylamino-carbonyl;

di($C_1$-$C_4$-alkyl)aminocarbonyl: di($C_1$-$C_2$-alkyl)aminocarbonyl as mentioned above and N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)-aminocarbonyl, N,N-di(1,1-dimethylethyl)aminocarbonyl, N-methyl-N-propyl-aminocarbonyl, N-methyl-N-(1-methylethyl)-aminocarbonyl, N-butyl-N-methylaminocarbonyl, N-methyl-N-(1-methylpropyl)aminocarbonyl, N-methyl-N-(2-methylpropyl)-aminocarbonyl, N-(1,1-dimethylethyl)-N-methylaminocarbonyl, N-ethyl-N-propylaminocarbonyl, N-ethyl-N-(1-methylethyl)-aminocarbonyl, N-butyl-N-ethylaminocarbonyl, N-ethyl-N-(1-methylpropyl)aminocarbonyl, N-ethyl-N-(2-methylpropyl)-aminocarbonyl, N-ethyl-N-(1,1-dimethylethyl)aminocarbonyl, N-(1-methylethyl)-N-propylaminocarbonyl, N-butyl-N-propylamino-carbonyl, N-(1-methylpropyl)-N-propylaminocarbonyl, N-(2-methylpropyl)-N-propylamino-carbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)amino-carbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl)-aminocarbonyl;

$C_1$-$C_2$-alkylsulfonylamino-$C_1$-$C_2$-alkyl: $C_1$-$C_2$-alkyl which is substituted by $C_1$-$C_2$-alkylsulfonylannino as mentioned above, for example methylsulfonylaminomethyl, ethylsulfonylaminomethyl, 2-methylsulfonylaminoethyl and 2-ethylsulfonylaminoethyl;

$C_1$-$C_4$-alkylsulfonylamino-$C_1$-$C_4$-alkyl: $C_1$-$C_2$-alkylsulfonylamino-$C_1$-$C_2$-alkyl as mentioned above, and propylsulfonylaminomethyl, (1-methylethylsulfonylamino)methyl, butylsulfonylaminomethyl, (1-methylpropyl-sulfonylamino)methyl, (2-methylpropyl-sulfonylamino)methyl, (1,1-dimethylethylsulfonylamino)-methyl, 2-(propylsulfonylamino)ethyl, 2-(1-methylethyl-sulfonylamino)ethyl, 2-(butylsulfonylamino)ethyl, 2-(1-methylpropylsulfonylamino)ethyl, 2-(2-methylpropylsulfonylamino)ethyl, 2-(1,1-dimethylethylsulfonylamino)ethyl, 2-(methylsulfonylamino)propyl, 3-(methylsulfonylamino)propyl, 2-(ethylsulfonylamino)propyl, 3-(ethylsulfonylamino)propyl, 3-(propylsulfonylamino)propyl, 3-(butylsulfonylamino)propyl, 4-(methylsulfonylamino)butyl, 4-(ethylsulfonylamino)butyl, 4-(propylsulfonylamino)butyl and 4-(butylsulfonylamino)butyl.

The compounds of components A), B) and, if desired C) as well as their salts, esters and amides, also may exist in the form of the pure enantiomere, and also as racemates or diastereomer mixtures.

Preferred with regard to the synergistic herbicidal action of the mixtures according to the invention are those sulfonylureas of formula II wherein the variables have the following meanings, either alone or in combination:

$R^1$ is hydrogen; or $C_1$-$C_3$-alkyl, especially methyl or ethyl, preferably methyl;

$R^2$ is halogen, especially fluorine or chlorine, especially chlorine; $C_1$-$C_3$-alkyl, especially methyl or ethyl, preferably methyl; $C_1$-$C_2$-haloalkyl, especially difluoromethyl or trifluoromethyl, preferably trifluoromethyl; $C_1$-$C_3$-alkoxy, especially methoxy or ethoxy, preferably methoxy; $C_1$-$C_2$-haloalkoxy, especially difluoromethoxy or trifluoromethoxy, preferably difluoromethoxy; $C_1$-$C_2$-alkylamino, especially methylamino; or di($C_1$-$C_2$-alkyl)amino, especially dimethylamino or diethylamino, preferably dimethylamino;

$R^3$ is $C_1$-$C_3$-alkyl, especially methyl or ethyl, preferably methyl; $C_1$-$C_3$-alkoxy, especially methoxy or ethoxy; or $C_1$-$C_2$-haloalkoxy especially difluoromethoxy, trifluoromethoxy or 2,2,2-trifluoroethoxy, preferably difluoromethoxy or 2,2,2-trifluoroethoxy;

$R^4$ is halogen, preferably fluorine, chlorine or bromine, especially chlorine; $C_1$-$C_3$-haloalkyl, especially difluoromethyl, trifluoromethyl, 2,2,2-trifluoroethyl or 3,3,3-trifluoropropyl, preferably trifluoromethyl or 3,3,3-trifluoropropyl; $C_1$-$C_3$-alkoxy, especially methoxy or ethoxy, preferably ethoxy; $C_1$-$C_2$-haloalkoxy, especially difluoromethoxy, 2-fluoroethoxy, 2-chloroethoxy, 2,2-difluoroethoxy or 2,2,2-trifluoroethoxy, preferably 2-chloroethoxy or 2,2,2-trifluoro-ethoxy; $C_1$-$C_2$-alkoxy-$C_1$-$C_2$-alkoxy, especially 2-methoxyethoxy or 2-ethoxyethoxy, preferably 2-methoxyethoxy; cyclopropylcarbonyl; di($C_1$-$C_2$-alkyl)aminocarbonyl, especially dimethyl-aminocarbonyl or diethylaminocarbonyl, preferably dimethylaminocarbonyl; or hydroxycarbonyl;

especially is halogen, preferably fluorine, chlorine or bromine, especially chlorine; $C_1$-$C_3$-haloalkyl, especially difluoromethyl, trifluoromethyl, 2,2,2-trifluoroethyl or 3,3,3-trifluoropropyl, preferably trifluoromethyl or 3,3,3-trifluoropropyl; $C_1$-$C_3$-alkoxy, especially methoxy or ethoxy, preferably ethoxy; $C_1$-$C_2$-haloalkoxy, especially difluoromethoxy, 2-fluoroethoxy, 2-chloroethoxy, 2,2-difluoroethoxy or 2,2,2-tri-fluoroethoxy, preferably 2-chloroethoxy or 2,2,2-trifluoroethoxy; cyclopropylcarbonyl; di($C_1$-$C_2$-alkyl)aminocarbonyl, especially dimethyl-aminocarbonyl or diethylaminocarbonyl, preferably dimethylaminocarbonyl; or hydroxycarbonyl;

$R^5$ is hydrogen; halogen, especially chlorine, bromine or iodine, preferably iodine; or $C_1$-$C_2$-alkylsulfonylamino-$C_1$-$C_2$-alkyl, especially methylsulfonylaminomethyl or ethylsulfonylaminomethyl, preferably methylsulfonylaminomethyl; especially is hydrogen;

$R^6$ is hydroxycarbonyl; or $C_1$-$C_3$-alkylsulfonyl, especially methylsulfonyl or ethylsulfonyl, preferably ethylsulfonyl;
$R^7$ is hydrogen; or $C_1$-$C_2$-haloalkyl, especially difluoromethyl or trifluoromethyl, preferably trifluoromethyl;
$R^8$ is hydroxycarbonyl;
$R^9$ is 2-methyl-tetrazol-5-yl or hydroxycarbonyl;
$R^{10}$ is hydrogen; or halogen, especially fluorine, chlorine or bromine, preferably chlorine;
$R^{11}$ is $C_1$-$C_3$-alkyl, especially methyl or ethyl, preferably methyl;
$R^{12}$ is halogen, especially chlorine or bromine, preferably chlorine; or $C_1$-$C_3$-alkylsulfonyl, especially methylsulfonyl or ethylsulfonyl, preferably ethylsulfonyl;
or one of its environmentally compatible salts or esters, especially $C_1$-$C_3$-alkyl or oxetan-3-yl ester, preferably methyl-, ethyl or oxetan-3-yl ester;

Especially preferred are sulfonylureas of formula II wherein
A is A1, wherein
$R^4$ is halogen, preferably chlorine; $C_1$-$C_3$-haloalkyl, preferably trifluoromethyl or 3,3,3-trifluoropropyl; $C_1$-$C_2$-alkoxy, preferably ethoxy; $C_1$-$C_2$-haloalkoxy, preferably 2-chloroethoxy or 2,2,2-trifluoroethoxy; $C_1$-$C_2$-alkoxy-$C_1$-$C_2$-alkoxy, preferably 2-methoxyethoxy; di($C_1$-$C_2$-alkyl)amino-carbonyl, preferably dimethylaminocarbonyl; hydroxycarbonyl or methoxy-carbonyl, ethoxycarbonyl or oxetan-3-yloxycarbonyl;
$R^5$ is hydrogen; halogen, preferably iodine; or $C_1$-$C_2$-alkylsulfonylamino-$C_1$-$C_2$-alkyl, preferably methylsulfonylaminomethyl;
B is —O—, —NH—, —CH$_2$— or a bond;
$R^1$ is hydrogen; or $C_1$-$C_2$-alkyl, especially methyl;
$R^2$ is halogen, preferably chlorine; $C_1$-$C_2$-alkyl, preferably methyl; $C_1$-$C_2$-haloalkyl, preferably trifluoromethyl; $C_1$-$C_2$-alkoxy, preferably methoxy; $C_1$-$C_2$-haloalkoxy, preferably difluoromethoxy; $C_1$-$C_2$-alkylamino, especially methylamino; or di($C_1$-$C_2$-alkyl)-amino, preferably dimethylamino;
$R^3$ is $C_1$-$C_2$-alkyl, preferably methyl; $C_1$-$C_3$-alkoxy, especially methoxy or ethoxy; or $C_1$-$C_2$-haloalkoxy, preferably difluoromethoxy or 2,2,2-trifluoroethoxy;
X is CH or N;
or one of its environmentally compatible salts;
Examples for these sulfonylureas are bensulfuron, especially bensulfuron methyl, chlorimuron, especially chlorimuron ethyl, chlorsulfuron, cinosulfuron, cyclosulfamuron, ethametsulfuron, especially ethametsulfuron methyl, ethoxysulfuron, flazasulfuron, iodosulfuron, especially iodosulfuron methyl, mesosulfuron, especially mesosulfuron methyl, metsulfuron, especially metsulfuron methyl, nicosulfuron, primisulfuron, especially primisulfuron methyl, prosulfuron, sulfometuron, especially sulfometuron methyl or oxasulfuron, triasulfuron, tribenuron, especially tribenuron methyl, triflusulfuron, especially triflusulfuron methyl, trifloxysulfuron or tritosulfuron; or their environmentally compatible salts;
Particularly preferred are chlorsulfuron, iodosulfuron, especially iodosulfuron methyl, mesosulfuron, especially mesosulfuron methyl, metsulfuron, especially metsulfuron methyl, prosulfuron, triasulfuron, tribenuron, especially tribenuron methyl, or tritosulfuron; or their environmentally compatible salts;
Extraordinary preferred is tritosulfuron or its environmentally compatible salts.

Also especially preferred are sulfonylureas of formula II wherein
A is A1, wherein
$R^4$ is halogen, preferably chlorine; $C_1$-$C_3$-haloalkyl, preferably trifluoromethyl or 3,3,3-trifluoropropyl; $C_1$-$C_2$-alkoxy, preferably ethoxy; $C_1$-$C_2$-haloalkoxy, preferably 2-chloroethoxy or 2,2,2-trifluoroethoxy; cyclopropylcarbonyl; di($C_1$-$C_2$-alkyl)amino-carbonyl, preferably dimethylaminocarbonyl; hydroxycarbonyl or methoxy-carbonyl, ethoxycarbonyl or oxetan-3-yloxycarbonyl;
$R^5$ is hydrogen;
B is —O—, —NH—, —CH$_2$— or a bond; preferably a bond; $R^1$ is hydrogen; or $C_1$-$C_2$-alkyl, especially methyl;
$R^2$ is halogen, preferably chlorine; $C_1$-$C_2$-alkyl, preferably methyl; $C_1$-$C_2$-haloalkyl, preferably trifluoromethyl; $C_1$-$C_2$-alkoxy, preferably methoxy; $C_1$-$C_2$-haloalkoxy, preferably difluoromethoxy; $C_1$-$C_2$-alkylamino, especially methylamino; or di($C_1$-$C_2$-alkyl)-amino, preferably dimethylamino;
$R^3$ is $C_1$-$C_2$-alkyl, preferably methyl; $C_1$-$C_3$-alkoxy, especially methoxy or ethoxy; or $C_1$-$C_2$-haloalkoxy, preferably difluoromethoxy or 2,2,2-trifluoroethoxy;
X is CH or N;
or one of its environmentally compatible salts;
Examples for these sulfonylureas are bensulfuron, especially bensulfuron methyl, chlorimuron, especially chlorimuron ethyl, chlorsulfuron, cyclosulfamuron, ethametsulfuron, especially ethametsulfuron methyl, ethoxysulfuron, flazasulfuron, metsulfuron, especially metsulfuron methyl, nicosulfuron, primisulfuron, especially primisulfuron methyl, prosulfuron, sulfometuron, especially sulfometuron methyl or oxasulfuron, triasulfuron, tribenuron, especially tribenuron methyl, triflusulfuron, especially triflusulfuron methyl, trifloxysulfuron or tritosulfuron; or their environmentally compatible salts;
Particularly preferred are chlorsulfuron, metsulfuron, especially metsulfuron methyl, prosulfuron, triasulfuron, tribenuron, especially tribenuron methyl, or tritosulfuron; or their environmentally compatible salts;
Also particularly preferred are bensulfuron, especially bensulfuron methyl, chlorimuron, especially chlorimuron ethyl, chlorsulfuron, cyclosulfamuron, ethametsulfuron, especially ethametsulfuron methyl, ethoxysulfuron, flazasulfuron, nicosulfuron, primisulfuron, especially prim isulfuron methyl, prosulfuron, sulfometuron, especially sulfometuron methyl or oxasulfuron, triasulfuron or triflusulfuron, especially triflusulfuron methyl, or their environmentally compatible salts;
Extraordinary preferred are chlorsulfuron, prosulfuron or triasulfuron or their environmentally compatible salts;
Also especially preferred are sulfonylureas of formula II wherein
A is A2, wherein
$R^6$ is $C_1$-$C_2$-alkylsulfonyl, preferably ethylsulfonyl; hydroxycarbonyl or methoxylcarbonyl;
$R^7$ is hydrogen or $C_1$-$C_2$-haloalkyl, preferably trifluoromethyl;
B is a bond;
$R^1$ is hydrogen;
$R^2$ is $C_1$-$C_2$-alkoxy, preferably methoxy;

$R^3$ is $C_1$-$C_2$-alkoxy, especially methoxy;
X is CH;
or one of its environmentally compatible salts;

Examples for these sulfonylureas are flupyrsulfuron, especially flupyrsulfuron methyl, or rimsulfuron; or their environmentally compatible salts;

Particularly preferred is flupyrsulfuron, especially flupyrsulfuron methyl, or its environmentally compatible salts.

Also especially preferred are sulfonylureas of formula II wherein
A is A2, wherein
  $R^6$ is $C_1$-$C_2$-alkylsulfonyl, preferably ethylsulfonyl; hydroxycarbonyl or methoxylcarbonyl;
  $R^7$ is hydrogen;
B is a bond;
$R^1$ is hydrogen;
$R^2$ is $C_1$-$C_2$-alkoxy, preferably methoxy;
$R^3$ is $C_1$-$C_2$-alkoxy, especially methoxy;
X is CH;
or one of its environmentally compatible salts;

Examples for these sulfonylureas are rimsulfuron; or its environmentally compatible salts;

Also especially preferred are sulfonylureas of formula II wherein
A is A3, wherein
  $R^8$ is hydroxycarbonyl or methoxycarbonyl;
B is a bond;
$R^1$ is hydrogen;
$R^2$ is $C_1$-$C_2$-alkyl, preferably methyl;
$R^3$ is $C_1$-$C_2$-alkoxy, especially methoxy;
X is CH;
or one of its environmentally compatible salts;

An example for these sulfonylureas is thifensulfuron, especially thifensulfuron methyl; or its environmentally compatible salts;

Also especially preferred are sulfonylureas of formula II wherein
A is A4, wherein
  $R^9$ is 2-methyl-tetrazol-5-yl, hydroxycarbonyl, methoxycarbonyl or ethoxycarbony;
  $R^{10}$ is hydrogen; or halogen, preferably chlorine;
  $R^{11}$ is $C_1$-$C_2$-alkyl, preferably methyl;
B is a bond;
$R^1$ is hydrogen;
$R^2$ is $C_1$-$C_2$-alkoxy, preferably methoxy;
$R^3$ is $C_1$-$C_2$-alkoxy, preferably methoxy;
X is CH;
or one of its environmentally compatible salts;

Examples for these sulfonylureas are azimsulfuron, halosulfuron, especially halosulfuron methyl, or pyrazosulfuron, especially pyrazosulfuron ethyl; or their environmentally compatible salts;

Also especially preferred are sulfonylureas of formula II wherein
A is A5, wherein
  $R^{12}$ is halogen, preferably chlorine; or $C_1$-$C_2$-alkylsulfonyl, preferably ethylsulfonyl;
B is a bond;
$R^1$ is hydrogen;
$R^2$ is $C_1$-$C_2$-alkoxy, preferably methoxy;
$R^3$ is $C_1$-$C_2$-alkoxy, especially methoxy;
X is CH;
or one of its environmentally compatible salts;

Examples for these sulfonylureas are imazosulfuron or sulfosulfuron; or their environmentally compatible salts;

Particularly preferred is sulfosulfuron, or its environmentally compatible salts.

Also especially preferred are sulfonylureas of formula II wherein
A is A5, wherein
  $R^{12}$ is halogen;
B is a bond;
$R^1$ is hydrogen;
$R^2$ is $C_1$-$C_2$-alkoxy, preferably methoxy;
$R^3$ is $C_1$-$C_2$-alkoxy, especially methoxy;
X is CH;
or one of its environmentally compatible salts;

Examples for these sulfonylureas are imazosulfuron or its environmentally compatible salts;

If desired, the synergistic mixtures according to the invention comprise as component C) a safener as mentioned at the outset.

Preferred compounds of the component C) are cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Preferred synergistic mixtures according to the invention comprise as component A) picolinafen and as component B) bensulfuron, especially bensulfuron methyl.

Also preferred are synergistic mixtures which comprise as component A) picolinafen, as component B) bensulfuron, especially bensulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) bensulfuron, especially bensulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) bensulfuron, especially bensulfuron methyl, and as component C) isoxadifen, preferably isoxadifen "acid" or isoxadifen ethyl.

Also especially preferred are synergistic mixtures which comprise as component A) picolinafen, as component B) bensulfuron, especially bensulfuron methyl, and as component C) mefenpyr, preferably mefenpyr "acid" or mefenpyr diethyl.

Also preferred are synergistic mixtures which comprise as component A) picolinafen and as component B) chlorimuron, especially chlorimuron ethyl.

Also preferred are synergistic mixtures which comprise as component A) picolinafen, as component B) chlorimuron, especially chlorimuron ethyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) chlorimuron, especially chlorimuron ethyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) chlorimuron, especially chlorimuron ethyl, and as component C) isoxadifen, preferably isoxadifen "acid" or isoxadifen ethyl Also especially preferred are synergistic mixtures which comprise as component A) picolinafen, as component B) chlorimuron, especially chlorimuron ethyl, and as component C) mefenpyr, preferably mefenpyr "acid" or mefenpyr diethyl.

Also preferred are synergistic mixtures which comprise as component A) picolinafen and as component B) chlorsulfuron.

Also preferred are synergistic mixtures which comprise as component A) picolinafen, as component B) chlorsulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) chlorsulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) chlorsulfuron, and as component C) isoxadifen, preferably isoxadifen "acid" or isoxadifen ethyl Also especially preferred are synergistic mixtures which comprise as component A) picolinafen, as component B) chlorsulfuron, and as component C) mefenpyr, preferably mefenpyr "acid" or mefenpyr diethyl.

Also preferred are synergistic mixtures which comprise as component A) picolinafen and as component B) cinosulfuron.

Also preferred are synergistic mixtures which comprise as component A) picolinafen, as component B) cinosulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) cinosulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) cinosulfuron, and as component C) isoxadifen, preferably isoxadifen "acid" or isoxadifen ethyl.

Also especially preferred are synergistic mixtures which comprise as component A) picolinafen, as component B) cinosulfuron, and as component C) mefenpyr, preferably mefenpyr "acid" or mefenpyr diethyl.

Also preferred are synergistic mixtures which comprise as component A) picolinafen and as component B) cyclosulfamuron.

Also preferred are synergistic mixtures which comprise as component A) picolinafen, as component B) cyclosulfamuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) cyclosulfamuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) cyclosulfamuron, and as component C) isoxadifen, preferably isoxadifen "acid" or isoxadifen ethyl Also especially preferred are synergistic mixtures which comprise as component A) picolinafen, as component B) cyclosulfamuron, and as component C) mefenpyr, preferably mefenpyr "acid" or mefenpyr diethyl.

Also preferred are synergistic mixtures which comprise as component A) picolinafen and as component B) ethametsulfuron, especially ethametsulfuron methyl.

Also preferred are synergistic mixtures which comprise as component A) picolinafen, as component B) ethametsulfuron, especially ethametsulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) ethametsulfuron, especially ethametsulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) ethametsulfuron, especially ethametsulfuron methyl, and as component C) isoxadifen, preferably isoxadifen "acid" or isoxadifen ethyl Also especially preferred are synergistic mixtures which comprise as component A) picolinafen, as component B) ethametsulfuron, especially ethametsulfuron methyl, and as component C) mefenpyr, preferably mefenpyr "acid" or mefenpyr diethyl.

Also preferred are synergistic mixtures which comprise as component A) picolinafen and as component B) ethoxysulfuron.

Also preferred are synergistic mixtures which comprise as component A) picolinafen, as component B) ethoxysulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) ethoxysulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) ethoxysulfuron, and as component C) isoxadifen, preferably isoxadifen "acid" or isoxadifen ethyl Also especially preferred are synergistic mixtures which comprise as component A) picolinafen, as component B) ethoxysulfuron, and as component C) mefenpyr, preferably mefenpyr "acid" or mefenpyr diethyl.

Also preferred are synergistic mixtures which comprise as component A) picolinafen and as component B) flazasulfuron.

Also preferred are synergistic mixtures which comprise as component A) picolinafen, as component B) flazasulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) flazasulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) flazasulfuron, and as component C) isoxadifen, preferably isoxadifen "acid" or isoxadifen ethyl Also especially preferred are synergistic mixtures which comprise as component A) picolinafen, as component B) flazasulfuron, and as component C) mefenpyr, preferably mefenpyr "acid" or mefenpyr diethyl.

Also preferred are synergistic mixtures which comprise as component A) picolinafen and as component B) iodosulfuron, especially iodosulfuron methyl, Also preferred are synergistic mixtures which comprise as component A) picolinafen, as component B) iodosulfuron, especially iodosulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) iodosulfuron, especially iodosulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) iodosulfuron, especially iodosulfuron methyl, and as component C) isoxadifen, preferably isoxadifen "acid" or isoxadifen ethyl.

Also especially preferred are synergistic mixtures which comprise as component A) picolinafen, as component B) iodosulfuron, especially iodosulfuron methyl, and as component C) mefenpyr, preferably mefenpyr "acid" or mefenpyr diethyl.

Also preferred are synergistic mixtures which comprise as component A) picolinafen and as component B) mesosulfuron, especially mesosulfuron methyl.

Also preferred are synergistic mixtures which comprise as component A) picolinafen, as component B) mesosulfuron, especially mesosulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) mesosulfuron, especially mesosulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) mesosulfuron, especially mesosulfuron methyl, and as component C) isoxadifen, preferably isoxadifen "acid" or isoxadifen ethyl Also especially preferred are synergistic mixtures which comprise as component A) picolinafen, as component B) mesosulfuron, especially mesosulfuron methyl, and as component C) mefenpyr, preferably mefenpyr "acid" or mefenpyr diethyl.

Also preferred are synergistic mixtures which comprise as component A) picolinafen and as component B) metsulfuron, especially metsulfuron methyl.

Also preferred are synergistic mixtures which comprise as component A) picolinafen, as component B) metsulfuron, especially metsulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) metsulfuron, especially metsulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) metsulfuron, especially metsulfuron methyl, and as component C) isoxadifen, preferably isoxadifen "acid" or isoxadifen ethyl Also especially preferred are synergistic mixtures which comprise as component A) picolinafen, as component B) metsulfuron, especially metsulfuron methyl, and as component C) mefenpyr, preferably mefenpyr "acid" or mefenpyr diethyl.

Also preferred are synergistic mixtures which comprise as component A) picolinafen and as component B) nicosulfuron.

Also preferred are synergistic mixtures which comprise as component A) picolinafen, as component B) nicosulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) nicosulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) nicosulfuron, and as component C) isoxadifen, preferably isoxadifen "acid" or isoxadifen ethyl Also especially preferred are synergistic mixtures which comprise as component A) picolinafen, as component B nicosulfuron, and as component C) mefenpyr, preferably mefenpyr "acid" or mefenpyr diethyl.

Also preferred are synergistic mixtures which comprise as component A) picolinafen and as component B) primisulfuron, especially primisulfuron methyl.

Also preferred are synergistic mixtures which comprise as component A) picolinafen, as component B) primisulfuron, especially primisulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) primisulfuron, especially primisulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) primisulfuron, especially primisulfuron methyl, and as component C) isoxadifen, preferably isoxadifen "acid" or isoxadifen ethyl.

Also especially preferred are synergistic mixtures which comprise as component A) picolinafen, as component B) primisulfuron, especially primisulfuron methyl, and as component C) mefenpyr, preferably mefenpyr "acid" or mefenpyr diethyl.

Also preferred are synergistic mixtures which comprise as component A) picolinafen and as component B) prosulfuron.

Also preferred are synergistic mixtures which comprise as component A) picolinafen, as component B) prosulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) prosulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) prosulfuron, and as component C) isoxadifen, preferably isoxadifen "acid" or isoxadifen ethyl Also especially preferred are synergistic mixtures which comprise as component A) picolinafen, as component B) prosulfuron, and as component C) mefenpyr, preferably mefenpyr "acid" or mefenpyr diethyl.

Also preferred are synergistic mixtures which comprise as component A) picolinafen and as component B) sulfometuron, especially sulfometuron methyl or oxasulfuron.

Also preferred are synergistic mixtures which comprise as component A) picolinafen, as component B) sulfometuron, especially sulfometuron methyl or oxasulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) sulfometuron, especially sulfometuron methyl or oxasulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) sulfometuron, especially sulfometuron methyl or oxasulfuron, and as component C) isoxadifen, preferably isoxadifen "acid" or isoxadifen ethyl Also especially preferred are synergistic mixtures which comprise as component A) picolinafen, as component B) sulfometuron, especially sulfometuron methyl or oxasulfuron, and as component C) mefenpyr, preferably mefenpyr "acid" or mefenpyr diethyl.

Also preferred are synergistic mixtures which comprise as component A) picolinafen and as component B) triasulfuron.

Also preferred are synergistic mixtures which comprise as component A) picolinafen, as component B) triasulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) triasulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) triasulfuron, and as component C) isoxadifen, preferably isoxadifen "acid" or isoxadifen ethyl.

Also especially preferred are synergistic mixtures which comprise as component A) picolinafen, as component B) triasulfuron, and as component C) mefenpyr, preferably mefenpyr "acid" or mefenpyr diethyl.

Also preferred are synergistic mixtures which comprise as component A) picolinafen and as component B) tribenuron, especially tribenuron methyl.

Also preferred are synergistic mixtures which comprise as component A) picolinafen, as component B) tribenuron, especially tribenuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) tribenuron, especially tribenuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) tribenuron, especially tribenuron methyl, and as component C) isoxadifen, preferably isoxadifen "acid" or isoxadifen ethyl Also especially preferred are synergistic mixtures which comprise as component A) picolinafen, as component B) tribenuron, especially tribenuron methyl, and as component C) mefenpyr, preferably mefenpyr "acid" or mefenpyr diethyl.

Also preferred are synergistic mixtures which comprise as component A) picolinafen and as component B) triflusulfuron, especially triflusulfuron methyl.

Also preferred are synergistic mixtures which comprise as component A) picolinafen, as component B) triflusulfuron, especially triflusulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) triflusulfuron, especially triflusulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) triflusulfuron, especially triflusulfuron methyl, and as component C) isoxadifen, preferably isoxadifen "acid" or isoxadifen ethyl Also especially preferred are synergistic mixtures which comprise as component A) picolinafen, as component B) triflusulfuron, especially triflusulfuron methyl, and as component C) mefenpyr, preferably mefenpyr "acid" or mefenpyr diethyl.

Also preferred are synergistic mixtures which comprise as component A) picolinafen and as component B) trifloxysulfuron.

Also preferred are synergistic mixtures which comprise as component A) picolinafen, as component B) trifloxysulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) trifloxysulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) trifloxysulfuron, and as component C) isoxadifen, preferably isoxadifen "acid" or isoxadifen ethyl Also especially preferred are synergistic mixtures which comprise as component A) picolinafen, as component B) trifloxysulfuron, and as component C) mefenpyr, preferably mefenpyr "acid" or mefenpyr diethyl.

Also preferred are synergistic mixtures which comprise as component A) picolinafen and as component B) tritosulfuron.

Also preferred are synergistic mixtures which comprise as component A) picolinafen, as component B) tritosulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) tritosulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) tritosulfuron, and as component C) isoxadifen, preferably isoxadifen "acid" or isoxadifen ethyl.

Also especially preferred are synergistic mixtures which comprise as component A) picolinafen, as component B) tritosulfuron, and as component C) mefenpyr, preferably mefenpyr "acid" or mefenpyr diethyl.

Also preferred are synergistic mixtures which comprise as component A) picolinafen and as component B) flupyrsulfuron, especially flupyrsulfuron methyl.

Also preferred are synergistic mixtures which comprise as component A) picolinafen, as component B) flupyrsulfuron, especially flupyrsulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) flupyrsulfuron, especially flupyrsulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) flupyrsulfuron, especially flupyrsulfuron methyl, and as component C) isoxadifen, preferably isoxadifen "acid" or isoxadifen ethyl.

Also especially preferred are synergistic mixtures which comprise as component A) picolinafen, as component B) flupyrsulfuron, especially flupyrsulfuron methyl, and as component C) mefenpyr, preferably mefenpyr "acid" or mefenpyr diethyl.

Also preferred are synergistic mixtures which comprise as component A) picolinafen and as component B) rimsulfuron.

Also preferred are synergistic mixtures which comprise as component A) picolinafen, as component B) rimsulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) rimsulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) rimsulfuron, and as component C) isoxadifen, preferably isoxadifen "acid" or isoxadifen ethyl.

Also especially preferred are synergistic mixtures which comprise as component A) picolinafen, as component B) rimsulfuron, and as component C) mefenpyr, preferably mefenpyr "acid" or mefenpyr diethyl.

Also preferred are synergistic mixtures which comprise as component A) picolinafen and as component B) thifensulfuron, especially thifensulfuron methyl.

Also preferred are synergistic mixtures which comprise as component A) picolinafen, as component B) thifensulfuron, especially thifensulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) thifensulfuron, especially thifensulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) thifensulfuron, especially thifensulfuron methyl, and as component C) isoxadifen, preferably isoxadifen "acid" or isoxadifen ethyl.

Also especially preferred are synergistic mixtures which comprise as component A) picolinafen, as component B) thifensulfuron, especially thifensulfuron methyl, and as component C) mefenpyr, preferably mefenpyr "acid" or mefenpyr diethyl.

Also preferred are synergistic mixtures which comprise as component A) picolinafen and as component B) azimsulfuron.

Also preferred are synergistic mixtures which comprise as component A) picolinafen, as component B) azimsulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) azimsulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) azimsulfuron, and as component C) isoxadifen, preferably isoxadifen "acid" or isoxadifen ethyl.

Also especially preferred are synergistic mixtures which comprise as component A) picolinafen, as component B) azimsulfuron, and as component C) mefenpyr, preferably mefenpyr "acid" or mefenpyr diethyl.

Also preferred are synergistic mixtures which comprise as component A) picolinafen and as component B) halosulfuron, especially halosulfuron methyl.

Also preferred are synergistic mixtures which comprise as component A) picolinafen, as component B) halosulfuron, especially halosulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) halosulfuron, especially halosulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) halosulfuron, especially halosulfuron methyl, and as component C) isoxadifen, preferably isoxadifen "acid" or isoxadifen ethyl.

Also especially preferred are synergistic mixtures which comprise as component A) picolinafen, as component B) halosulfuron, especially halosulfuron methyl, and as component C) mefenpyr, preferably mefenpyr "acid" or mefenpyr diethyl.

Also preferred are synergistic mixtures which comprise as component A) picolinafen and as component B) pyrazosulfuron, especially pyrazosulfuron methyl.

Also preferred are synergistic mixtures which comprise as component A) picolinafen, as component B) pyrazosulfuron, especially pyrazosulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) pyrazosulfuron, especially pyrazosulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) pyrazosulfuron, especially pyrazosulfuron methyl, and as component C) isoxadifen, preferably isoxadifen "acid" or isoxadifen ethyl.

Also especially preferred are synergistic mixtures which comprise as component A) picolinafen, as component B) pyrazosulfuron, especially pyrazosulfuron methyl, and as component C) mefenpyr, preferably mefenpyr "acid" or mefenpyr diethyl.

Also preferred are synergistic mixtures which comprise as component A) picolinafen and as component B) imazosulfuron.

Also preferred are synergistic mixtures which comprise as component A) picolinafen, as component B) imazosulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) imazosulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) imazosulfuron, and as component C) isoxadifen, preferably isoxadifen "acid" or isoxadifen ethyl.

Also especially preferred are synergistic mixtures which comprise as component A) picolinafen, as component B) imazosulfuron, and as component C) mefenpyr, preferably mefenpyr "acid" or mefenpyr diethyl.

Also preferred are synergistic mixtures which comprise as component A) picolinafen and as component B) sulfosulfuron.

Also preferred are synergistic mixtures which comprise as component A) picolinafen, as component B) sulfosulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) sulfosulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) sulfosulfuron, and as component C) isoxadifen, preferably isoxadifen "acid" or isoxadifen ethyl.

Also especially preferred are synergistic mixtures which comprise as component A) picolinafen, as component B) sulfosulfuron, and as component C) mefenpyr, preferably mefenpyr "acid" or mefenpyr diethyl.

Also preferred are synergistic mixtures which comprise as component A) picolinafen and as component B) mesosulfuron, especially mesosulfuron methyl, and iodosulfuron, especially iodosulfuron methyl.

Also preferred are synergistic mixtures which comprise as component A) picolinafen, as component B) mesosulfuron, especially mesosulfuron methyl, and iodosulfuron, especially iodosulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) mesosulfuron, especially mesosulfuron methyl, and iodosulfuron, especially iodosulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) picolinafen, as component B) mesosulfuron, especially mesosulfuron methyl, and iodosulfuron, especially iodosulfuron methyl, and as component C) isoxadifen, preferably isoxadifen "acid" or isoxadifen ethyl.

Also especially preferred are synergistic mixtures which comprise as component A) picolinafen, as component B) mesosulfuron, especially mesosulfuron methyl, and iodosulfuron, especially iodosulfuron methyl, and as component C) mefenpyr, preferably mefenpyr "acid" or mefenpyr diethyl.

Also preferred are synergistic mixtures which comprise as component A) picolinafen and as component B) flupyrsulfuron, especially flupyrsulfuron methyl, and metsulfuron, especially metsulfuron methyl.

Also preferred are synergistic mixtures which comprise as component A) picolinafen, as component B) flupyrsulfuron, especially flupyrsulfuron methyl, and metsulfuron, especially metsulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) flupyrsulfuron, especially flupyrsulfuron methyl, and metsulfuron, especially metsulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) flupyrsulfuron, especially flupyrsulfuron methyl, and metsulfuron, especially metsulfuron methyl, and as component C) isoxadifen, preferably isoxadifen "acid" or isoxadifen ethyl.

Also especially preferred are synergistic mixtures which comprise as component A) flupyrsulfuron, especially flupyrsulfuron methyl, and metsulfuron, especially metsulfuron methyl and as component C) mefenpyr, preferably mefenpyr "acid" or mefenpyr diethyl.

Also preferred are synergistic mixtures which comprise as component A) picolinafen and as component B) flupyrsulfuron, especially flupyrsulfuron methyl, and thifensulfuron, especially thifensulfuron methyl.

Also preferred are synergistic mixtures which comprise as component A) picolinafen, as component B) flupyrsulfuron, especially flupyrsulfuron methyl, and thifensulfuron, especially thifensulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) flupyrsulfuron, especially flupyrsulfuron methyl, and thifensulfuron, especially thifensulfuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) flupyrsulfuron, especially flupyrsulfuron methyl, and thifensulfuron, especially thifensulfuron methyl, and as component C) isoxadifen, preferably isoxadifen "acid" or isoxadifen ethyl.

Also especially preferred are synergistic mixtures which comprise as component A) flupyrsulfuron, especially flupyrsulfuron methyl, and thifensulfuron, especially thifensulfuron methyl, and as component C) mefenpyr, preferably mefenpyr "acid" or mefenpyr diethyl.

Also preferred are synergistic mixtures which comprise as component A) picolinafen and as component B) flupyrsulfuron, especially flupyrsulfuron methyl, and chlorsulfuron.

Also preferred are synergistic mixtures which comprise as component A) picolinafen, as component B) flupyrsulfuron, especially flupyrsulfuron methyl, and chlorsulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) flupyrsulfuron, especially flupyrsulfuron methyl, and chlorsulfuron and as component C) cloquintocet, preferably cloquintocet "acid", cloquintocet mexyl or cloquintocet mexyl x n hydrate (n=2 to 6).

Also especially preferred are synergistic mixtures which comprise as component A) flupyrsulfuron, especially flupyrsulfuron methyl, and chlorsulfuron and as component C) isoxadifen, preferably isoxadifen "acid" or isoxadifen ethyl.

Also especially preferred are synergistic mixtures which comprise as component A) flupyrsulfuron, especially flupyrsulfuron methyl, and chlorsulfuron, and as component C) mefenpyr, preferably mefenpyr "acid" or mefenpyr diethyl.

Also preferred are synergistic mixtures which comprise as component A) picolinafen and as component B) metsulfuron, especially metsulfuron methyl, and thifensulfuron, especially thifensulfuron methyl.

Also preferred are synergistic mixtures which comprise as component A) picolinafen, as component B) metsulfuron, especially metsulfuron methyl, and thifensulfuron, especially thifensulfuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) metsulfuron, especially metsulfuron methyl, and thifensulfuron, especially thifensulfuron methyl and as component C) cloquintocet, preferably cloquintocet "acid", cloquintocet mexyl or cloquintocet mexyl x n hydrate (n=2 to 6).

Also especially preferred are synergistic mixtures which comprise as component A) metsulfuron, especially metsulfuron methyl, and thifensulfuron, especially thifensulfuron methyl, and as component C) isoxadifen, preferably isoxadifen "acid" or isoxadifen ethyl.

Also especially preferred are synergistic mixtures which comprise as component A) metsulfuron, especially metsulfuron methyl, and thifensulfuron, especially thifensulfuron methyl, and as component C) mefenpyr, preferably mefenpyr "acid" or mefenpyr diethyl.

Also preferred are synergistic mixtures which comprise as component A) picolinafen and as component B) metsulfuron, especially metsulfuron methyl, and chlorsulfuron.

Also preferred are synergistic mixtures which comprise as component A) picolinafen, as component B) metsulfuron, especially metsulfuron methyl, and chlorsulfuron, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) metsulfuron, especially metsulfuron methyl, and chlorsulfuron, and as component C) cloquintocet, preferably cloquintocet "acid", cloquintocet mexyl or cloquintocet mexyl x n hydrate (n=2 to 6).

Also especially preferred are synergistic mixtures which comprise as component A) metsulfuron, especially metsulfuron methyl, and chlorsulfuron, and as component C) isoxadifen, preferably isoxadifen "acid" or isoxadifen ethyl.

Also especially preferred are synergistic mixtures which comprise as component A) metsulfuron, especially metsulfuron methyl, and chlorsulfuron, and as component C) mefenpyr, preferably mefenpyr "acid" or mefenpyr diethyl.

Also preferred are synergistic mixtures which comprise as component A) picolinafen and as component B) thifensulfuron, especially thifensulfuron methyl, and tribenuron, especially tribenuron methyl.

Also preferred are synergistic mixtures which comprise as component A) picolinafen, as component B) thifensulfuron, especially thifensulfuron methyl, and tribenuron, especially tribenuron methyl, and as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component A) picolinafen, as component B) thifensulfuron, especially thifensulfuron methyl, and tribenuron, especially tribenuron methyl, and as component C) cloquintocet, preferably cloquintocet "acid", cloquintocet mexyl or cloquintocet mexyl x n hydrate (n=2 to 6).

Also especially preferred are synergistic mixtures which comprise as component A) thifensulfuron, especially thifensulfuron methyl, and tribenuron, especially tribenuron methyl, and as component C) isoxadifen, preferably isoxadifen "acid" or isoxadifen ethyl.

Also especially preferred are synergistic mixtures which comprise as component A) thifensulfuron, especially thifensulfuron methyl, and tribenuron, especially tribenuron methyl, and as component C) mefenpyr, preferably mefenpyr "acid" or mefenpyr diethyl.

Moreover it may be advantageous that the synergistic mixture according to the present invention comprises as active ingredients a compound of group A), at least a compound of group B), if desired at least a compound of group C), and furthermore at least a herbicide of group D).

Examples of suitable herbicides of group D) are, inter alia, acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

Special examples of herbicides of group D) which can be used, are inter alia,
D1 acetyl-CoA carboxylase inhibitors (ACC), for example
  cyclohexenone oxime ethers, such as alloxydim, clethodim, cloproxydim, cycloxydim, sethoxydim, tralkoxydim, butroxydim, clefoxydim or tepraloxydim;
  phenoxyphenoxypropionic esters, such as clodinafop-propargyl, cyhalofopbutyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
  arylaminopropionic acids, such as flamprop-methyl or flamprop-isopropyl;
D2 acetolactate synthase inhibitors (ALS), for example
  imidazolinones, such as imazapyr, imazaquin, imazamethabenz-methyl (imazame), imazamox, imazapic or imazethapyr;
  pyrimidyl ethers, such as pyrithiobac-acid, pyrithiobac-sodium, bispyribac-sodium, KIH-6127 or pyribenzoxym;
  sulfonamides, such as cloransulam, diclosulam, florasulam, flumetsulam, metosulam or penoxsulam; or
  flucarbazone or propoxycarbazone;
D3 amides, for example
  allidochlor (CDAA), benzoylprop-ethyl, bromobutide, chlorthiamid, diphenamid, etobenzanid (benzchlomet), fluthiamide, fosamin or monalide;
D4 auxin herbicides, for example
  pyridinecarboxylic acids, such as clopyralid or picloram; or
  2,4-D or benazolin;
D5 auxin transport inhibitors, for example
  naptalame or diflufenzopyr;
D6 carotenoid biosynthesis inhibitors, for example
  benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;
D7 enolpyruvylshikimate-3-phosphate synthase inhibitors (EPSPS), for example
  glyphosate or sulfosate;
D8 glutamine synthetase inhibitors, for example
  bilanafos (bialaphos) or glufosinate-ammonium;
D9 lipid biosynthesis inhibitors, for example
  anilides, such as anilofos or mefenacet;
  chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchior, thenylchloror xylachlor;
  thioureas, such as butylate, cycloate, di-allate, dimepiperate, EPTC, esprocarb, molinate, pebulate, prosulfocarb, thiobencarb (benthiocarb), tri-allate or vernolate; or
  benfuresate or perfluidone;
D10 mitosis inhibitors, for example
  carbamates, such as asulam, carbetamid, chlorpropham, orbencarb, pronamid (propyzamid), propham or tiocarbazil;
  dinitroanilines, such as benefin, butralin, dinitramin, ethalfluralin, fluchioralin, oryzalin, pendimethalin, prodiamine or trifluralin;
  pyridines, such as dithiopyr or thiazopyr; or
  butamifos, chlorthal-dimethyl (DCPA) or maleic hydrazide;

D11 protoporphyrinogen IX oxidase inhibitors, for example
- diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
- oxadiazoles, such as oxadiargyl or oxadiazon;
- cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
- pyrazoles, such as ET-751, JV 485 or nipyraclofen;

D12 photosynthesis inhibitors, for example
- propanil, pyridate or pyridafol;
- benzothiadiazinones, such as bentazone;
- dinitrophenols, for example bromofenoxim, dinoseb, dinoseb-acetate, dinoterb or DNOC;
- dipyridylenes, such as cyperquat-chloride, difenzoquat-methylsulfate, diquat or paraquat-dichloride;
- ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
- phenols, such as bromoxynil or ioxynil;
- chloridazon;
- triazines, such as ametryn, atrazine, cyanazine, desmetryn, dimethamethryn, hexazinone, prometon, prometryn, propazine, simazine, simetryn, terbumeton, terbutryn, terbutylazine or trietazine;
- triazinones, such as metamitron or metribuzin;
- uracils, such as bromacil, lenacil or terbacil; or
- biscarbamates, such as desmedipham or phenmedipham;

D13 synergists, for example
- oxiranes, such as tridiphane;

D14 growth substances, for example
- aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
- benzoic acids, such as chloramben or dicamba; or
- quinolinecarboxylic acids, such as quinclorac or quinmerac;

D15 cell wall synthesis inhibitors, for example
- isoxaben or dichlobenil;

D16 various other herbicides, for example
- dichloropropionic acids, such as dalapon;
- dihydrobenzofurans, such as ethofumesate;
- phenylacetic acids, such as chlorfenac (fenac); or
- aziprotryn, barban, bensulide, benzthiazuron, benzo-fluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;

or their environmentally compatible salts, "acids", esters and amides.

Suitable salts, esters and amides are similar to those mentioned for the compounds of groups A), B) and C).

The compounds of group D) as well as their salts, "acids", esters and amides, may also exist in the form of the pure enantiomere, and also as racemates or diastereomer mixtures.

Preferred are synergistic mixtures which comprise as component A) picolinafen, a compound of group B) and a herbicide selected of the groups D1 to D16:

D1 acetyl-CoA carboxylase inhibitors (ACC), for example
- cyclohexenone oxime ethers, such as alloxydim, clethodim, cloproxydim, cycloxydim, sethoxydim, tralkoxydim, butroxydim, clefoxydim or tepraloxydim;
- phenoxyphenoxypropionic esters, such as clodinafop-propargyl, cyhalofopbutyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
- arylaminopropionic acids, such as flamprop-methyl or flamprop-isopropyl;

D2 acetolactate synthase inhibitors (ALS), for example
- imidazolinones, such as imazapyr, imazaquin, imazamethabenz-methyl (imazame), imazamox, imazapic or imazethapyr;
- pyrimidyl ethers, such as pyrithiobac-acid, pyrithiobac-sodium, bispyribac-sodium, KIH-6127 or pyribenzoxym;
- sulfonamides, such as cloransulam, diclosulam, florasulam, flumetsulam, metosulam or penoxsulam; or D3 amides, for example
- allidochlor (CDAA), benzoylprop-ethyl, bromobutide, chlorthiamid, diphenamid, etobenzanid (benzchlomet), fluthiamide, fosamin or monalide;

D4 auxin herbicides, for example
- pyridinecarboxylic acids, such as clopyralid or picloram; or
- 2,4-D or benazolin;

D5 auxin transport inhibitors, for example
- naptalame or diflufenzopyr;

D6 carotenoid biosynthesis inhibitors, for example
- benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

D7 enolpyruvylshikimate-3-phosphate synthase inhibitors (EPSPS), for example
- glyphosate or sulfosate;

D8 glutamine synthetase inhibitors, for example
- bilanafos (bialaphos) or glufosinate-ammonium;

D9 lipid biosynthesis inhibitors, for example
- anilides, such as anilofos or mefenacet;
- chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchloror xylachlor;
- thioureas, such as butylate, cycloate, di-allate, dimepiperate, EPTC, esprocarb, molinate, pebulate, prosulfocarb, thiobencarb (benthiocarb), tri-allate or vernolate; or
- benfuresate or perfluidone;

D10 mitosis inhibitors, for example
- carbamates, such as asulam, carbetamid, chlorpropham, orbencarb, pronamid (propyzamid), propham or tiocarbazil;
- dinitroanilines, such as benefin, butralin, dinitramin, ethalfluralin, fluchloralin, oryzalin, pendimethalin, prodiamine or trifluralin;
- pyridines, such as dithiopyr or thiazopyr; or
- butamifos, chlorthal-dimethyl (DCPA) or maleic hydrazide;

D11 protoporphyrinogen IX oxidase inhibitors, for example
- diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
- oxadiazoles, such as oxadiargyl or oxadiazon;
- cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
- pyrazoles, such as ET-751, JV 485 or nipyraclofen;

D12 photosynthesis inhibitors, for example
- propanil, pyridate or pyridafol;
- benzothiadiazinones, such as bentazone;
- dinitrophenols, for example bromofenoxim, dinoseb, dinoseb-acetate, dinoterb or DNOC;
- dipyridylenes, such as cyperquat-chloride, difenzoquat-methylsulfate, diquat or paraquat-dichloride;
- ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
- phenols, such as bromoxynil or ioxynil;
- chloridazon;
- triazines, such as ametryn, atrazine, cyanazine, desmetryn, dimethamethryn, hexazinone, prometon, prometryn, propazine, simazine, simetryn, terbumeton, terbutryn, terbutylazine or trietazine;
- triazinones, such as metamitron or metribuzin;
- uracils, such as bromacil, lenacil or terbacil; or
- biscarbamates, such as desmedipham or phenmedipham;

D13 synergists, for example
- oxiranes, such as tridiphane;

D14 growth substances, for example
- aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
- benzoic acids, such as chloramben or dicamba; or
- quinolinecarboxylic acids, such as quinclorac or quinmerac;

D15 cell wall synthesis inhibitors, for example
- isoxaben or dichlobenil;

D16 various other herbicides, for example
- dichloropropionic acids, such as dalapon;
- dihydrobenzofurans, such as ethofumesate;
- phenylacetic acids, such as chlorfenac (fenac); or
- aziprotryn, barban, bensulide, benzthiazuron, benzo-fluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;

or their environmentally compatible salts, "acids", esters and amides.

Also preferred are synergistic mixtures which comprise as component A) picolinafen, a compound of group B), as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl and a herbicide selected of the groups D1 to D16:

D1 acetyl-CoA carboxylase inhibitors (ACC), for example
- cyclohexenone oxime ethers, such as alloxydim, clethodim, cloproxydim, cycloxydim, sethoxydim, tralkoxydim, butroxydim, clefoxydim or tepraloxydim;
- phenoxyphenoxypropionic esters, such as clodinafop-propargyl, cyhalofopbutyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
- arylaminopropionic acids, such as flamprop-methyl or flamprop-isopropyl;

D2 acetolactate synthase inhibitors (ALS), for example
- imidazolinones, such as imazapyr, imazaquin, imazamethabenz-methyl (imazame), imazamox, imazapic or imazethapyr;
- pyrimidyl ethers, such as pyrithiobac-acid, pyrithiobac-sodium, bispyribac-sodium, KIH-6127 or pyribenzoxym;
- sulfonamides, such as cloransulam, diclosulam, florasulam, flumetsulam, metosulam or penoxsulam; or
- flucarbazone or propoxycarbazone;

D3 amides, for example
- allidochlor (CDAA), benzoylprop-ethyl, bromobutide, chlorthiamid, diphenamid, etobenzanid (benzchlomet), fluthiamide, fosamin or monalide;

D4 auxin herbicides, for example
- pyridinecarboxylic acids, such as clopyralid or picloram; or
- 2,4-D or benazolin;

D5 auxin transport inhibitors, for example
- naptalame or diflufenzopyr;

D6 carotenoid biosynthesis inhibitors, for example
- benzofenap, clomazone (dimethazone), diflufenican, fluorochloridone, fluridone, pyrazolynate, pyrazoxyfen, isoxaflutole, isoxachiortole, mesotrione, sulcotrione (chlormesulone), ketospiradox, flurtamone, norflurazon or amitrol;

D7 enolpyruvylshikimate-3-phosphate synthase inhibitors (EPSPS), for example
- glyphosate or sulfosate;

D8 glutamine synthetase inhibitors, for example
- bilanafos (bialaphos) or glufosinate-ammonium;

D9 lipid biosynthesis inhibitors, for example
- anilides, such as anilofos, flufenacet or mefenacet;
- chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchloror xylachlor;
- thioureas, such as butylate, cycloate, di-allate, dimepiperate, EPTC, esprocarb, molinate, pebulate, prosulfocarb, thiobencarb (benthiocarb), tri-allate or vernolate; or
- benfuresate or perfluidone;

D10 mitosis inhibitors, for example
- carbamates, such as asulam, carbetamid, chlorpropham, orbencarb, pronamid (propyzamid), propham or tiocarbazil;
- dinitroanilines, such as benefin, butralin, dinitramin, ethalfluralin, fluchloralin, oryzalin, pendimethalin, prodiamine or trifluralin;
- pyridines, such as dithiopyr or thiazopyr; or
- butamifos, chlorthal-dimethyl (DCPA) or maleic hydrazide;

D11 protoporphyrinogen IX oxidase inhibitors, for example
- diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
- oxadiazoles, such as oxadiargyl or oxadiazon;
- cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
- pyrazoles, such as ET-751, JV 485 or nipyraclofen;

D12 photosynthesis inhibitors, for example
- propanil, pyridate or pyridafol;
- benzothiadiazinones, such as bentazone;
- dinitrophenols, for example bromofenoxim, dinoseb, dinoseb-acetate, dinoterb or DNOC;
- dipyridylenes, such as cyperquat-chloride, difenzoquat-methylsulfate, diquat or paraquat-dichloride;
- ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
- phenols, such as bromoxynil or ioxynil;
- chloridazon;
- triazines, such as ametryn, atrazine, cyanazine, desmetryn, dimethamethryn, hexazinone, prometon, prometryn, propazine, simazine, simetryn, terbumeton, terbutryn, terbutylazine or trietazine;
- triazinones, such as metamitron or metribuzin;
- uracils, such as bromacil, lenacil or terbacil; or
- biscarbamates, such as desmedipham or phenmedipham;

D13 synergists, for example
- oxiranes, such as tridiphane;

D14 growth substances, for example
- aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
- benzoic acids, such as chloramben or dicamba; or
- quinolinecarboxylic acids, such as quinclorac or quinmerac;

D15 cell wall synthesis inhibitors, for example
- isoxaben or dichlobenil;

D16 various other herbicides, for example
- dichloropropionic acids, such as dalapon;
- dihydrobenzofurans, such as ethofumesate;
- phenylacetic acids, such as chlorfenac (fenac); or
- aziprotryn, barban, bensulide, benzthiazuron, benzo-fluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;

or their environmentally compatible salts, "acids", esters and amides.

Also preferred are synergistic mixtures which comprise as component A) picolinafen, a compound of group B), as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl and a herbicide selected of the groups D1 to D16:

D1 acetyl-CoA carboxylase inhibitors (ACC), for example
- cyclohexenone oxime ethers, such as alloxydim, clethodim, cloproxydim, cycloxydim, sethoxydim, tralkoxydim, butroxydim, clefoxydim or tepraloxydim;
- phenoxyphenoxypropionic esters, such as clodinafop-propargyl, cyhalofopbutyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
- arylaminopropionic acids, such as flamprop-methyl or flamprop-isopropyl;

D2 acetolactate synthase inhibitors (ALS), for example
- imidazolinones, such as imazapyr, imazaquin, imazamethabenz-methyl (imazame), imazamox, imazapic or imazethapyr;
- pyrimidyl ethers, such as pyrithiobac-acid, pyrithiobac-sodium, bispyribac-sodium, KIH-6127 or pyribenzoxym;
- sulfonamides, such as cloransulam, diclosulam, florasulam, flumetsulam, metosulam or penoxsulam;

D3 amides, for example
- allidochlor (CDAA), benzoylprop-ethyl, bromobutide, chlorthiamid, diphenamid, etobenzanid (benzchlomet), fluthiamide, fosamin or monalide;

D4 auxin herbicides, for example
- pyridinecarboxylic acids, such as clopyralid or picloram; or
- 2,4-D or benazolin;

D5 auxin transport inhibitors, for example
- naptalame or diflufenzopyr;

D6 carotenoid biosynthesis inhibitors, for example
- benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

D7 enolpyruvylshikimate-3-phosphate synthase inhibitors (EPSPS), for example
- glyphosate or sulfosate;

D8 glutamine synthetase inhibitors, for example
- bilanafos (bialaphos) or glufosinate-ammonium;

D9 lipid biosynthesis inhibitors, for example
- anilides, such as anilofos or mefenacet;
- chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchloror xylachlor;
- thioureas, such as butylate, cycloate, di-allate, dimepiperate, EPTC, esprocarb, molinate, pebulate, prosulfocarb, thiobencarb (benthiocarb), tri-allate or vernolate; or
- benfuresate or perfluidone;

D10 mitosis inhibitors, for example
- carbamates, such as asulam, carbetamid, chlorpropham, orbencarb, pronamid (propyzamid), propham or tiocarbazil;
- dinitroanilines, such as benefin, butralin, dinitramin, ethalfluralin, fluchloralin, oryzalin, pendimethalin, prodiamine or trifluralin;
- pyridines, such as dithiopyr or thiazopyr; or
- butamifos, chlorthal-dimethyl (DCPA) or maleic hydrazide;

D11 protoporphyrinogen IX oxidase inhibitors, for example
  diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
  oxadiazoles, such as oxadiargyl or oxadiazon;
  cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
  pyrazoles, such as ET-751, JV 485 or nipyraclofen;
D12 photosynthesis inhibitors, for example
propanil, pyridate or pyridafol;
benzothiadiazinones, such as bentazone;
dinitrophenols, for example bromofenoxim, dinoseb, dinoseb-acetate, dinoterb or DNOC;
dipyridylenes, such as cyperquat-chloride, difenzoquat-methylsulfate, diquat or paraquat-dichloride;
ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
phenols, such as bromoxynil or ioxynil;
chloridazon;
triazines, such as ametryn, atrazine, cyanazine, desmetryn, dimethamethryn, hexazinone, prometon, prometryn, propazine, simazine, simetryn, terbumeton, terbutryn, terbutylazine or trietazine;
triazinones, such as metamitron or metribuzin;
uracils, such as bromacil, lenacil or terbacil; or
biscarbamates, such as desmedipham or phenmedipham;
D13 synergists, for example
oxiranes, such as tridiphane;
D14 growth substances, for example
aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
benzoic acids, such as chloramben or dicamba; or
quinolinecarboxylic acids, such as quinclorac or quinmerac;
D15 cell wall synthesis inhibitors, for example
isoxaben or dichlobenil;
D16 various other herbicides, for example
dichloropropionic acids, such as dalapon;
dihydrobenzofurans, such as ethofumesate;
phenylacetic acids, such as chlorfenac (fenac); or
aziprotryn, barban, bensulide, benzthiazuron, benzo-fluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;
or their environmentally compatible salts, "acids", esters and amides.

Also preferred are synergistic mixtures which comprise as component A) picolinafen, as component B) tritosulfuron and as component D) flucarbazone. Also preferred are synergistic mixtures which comprise as component A) picolinafen, as component B) tritosulfuron, as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl, and as component D) flucarbazone.

Also preferred are synergistic mixtures which comprise as component A) picolinafen, as component B) tritosulfuron and as component D) propoxycarbazone.

Also preferred are synergistic mixtures which comprise as component A) picolinafen, as component B) tritosulfuron, as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl, and as component D) propoxycarbazone.

Also preferred are synergistic mixtures which comprise as component A) picolinafen, as component B) triasulfuron and as component D) dicamba.

Also preferred are synergistic mixtures which comprise as component A) picolinafen, as component B) triasulfuron, as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl, and as component D) dicamba.

Also preferred are synergistic mixtures which comprise as component A) picolinafen, as component B) chlorsulfuron and as component D) dicamba.

Also preferred are synergistic mixtures which comprise as component A) picolinafen, as component B) chlorsulfuron, as component C) cloquintocet, preferably cloquintocet "acid", cloquintocet mexyl or cloquintocet mexyl x n hydrate (n=2 to 6); isoxadifen, preferably isoxadifen "acid" or isoxadifen ethyl; or mefenpyr, preferably mefenpyr "acid" or mefenpyr diethyl, and as component D) dicamba.

Preferred are synergistic mixtures which comprise as active ingredients only picolinafen and one compound of group B).

Especially preferred synergistic mixtures thereof are in analogy to the above-mentioned ones.

Also preferred are synergistic mixtures which comprise as active ingredients only picolinafen, one compound of group B) and one compound of group C).

Especially preferred synergistic mixtures thereof are in analogy to the above-mentioned ones.

Also preferred are synergistic mixtures which comprise as active ingredients only picolinafen, one compound of group B) and one compound of group D).

Especially preferred synergistic mixtures thereof are in analogy to the above-mentioned ones.

Also preferred are synergistic mixtures which comprise as active ingredients only picolinafen, one compound of group B), one compound of group C) and one compound of group D).

Especially preferred synergistic mixtures thereof are in analogy to the above-mentioned ones.

Picolinafen is disclosed in EP 447 004.

The compounds of group B) are described, for example, in "Herbizide [Herbicides]", Hock, Fedtke, Schmidt, 1st edition, Thieme 1995 ("azimsulfuron (DPX-A-8947)" p. 175, "bensulfuron" p. 31, "pyrazosulfuron" p. 31, "cinosulfuron" p. 31, "ethametsulfuron" p. 36, "thifensulfuron" p. 35;

"Short Review of Herbicides & PGRs 1991, Hodogaya Chemicals ("chlorimuron" p. 92, "chlorsulfuron" p. 92, "flazasulfuron" p. 96, "metsulfuron" S.92, "nicosulfuron" p. 96, "sulfometuron" p. 92, "triasulfuron" p. 94);

"Agricultural Chemicals", Book II Herbicides, 1993 (s. "imazosulfuron (TH-913)" p. 150, halosulfuron" p. 148, "rimsulfuron" p. 138, "tribenuron" p. 139, "triflusulfuron" p. 137, "primisulfuron" p. 147);

"Agricultural Chemicals", Book II Herbicides, 13$^{th}$ Edition (s. "sulfosulfuron" p. 145, "ethoxysulfuron" p. 149);

"Brighton Crop Protection Conference—Weeds—1993" (s. "prosulfuron" p. 53);

"Brighton Crop Protection Conference—Weeds—1995" (s. "flupyrsulfuron" p. 50);

"Brighton Crop Protection Conference—Weeds—1999" (s. "iodosulfuron" p. 16);

"The Pesticide Manual, 12$^{th}$ edition" ("cyclosulfamuron" p. 217);

"Agrow No. 347, Mar. 3$^{rd}$ 2000" ("mesosulfuron" p. 22);

"Farm Chemicals Handbook 2002" ("trifloxysulfuron" C405);

PCT/EP 96/03996 ("tritosulfuron").

The compounds of group C) are described, for example, in

"Herbizide [Herbicides]", Hock, Fedtke, Schmidt, 1st edition, Thieme 1995 ("dichlormid" p. 263, "benoxacor" p. 263, "LAB-145138" p. 263, "MG-191" p. 263, "MON-13900" p. 263, "cyometrinil" p. 265, "oxabetrinil" p. 265, "fluxofenim" p. 265, "flurazole" p. 265, "naphtalic acid anhydride" p. 265, "fenchlorim" p. 266, "fenchlorazol" p. 266, "cloquintocet" p. 266);

WO 91/07874 ("mefenpyr");

WO 99/00020 ("1-ethyl-4-hydroxy-3-(1H-tetrazol-5-yl)-1H-quinolin-2-one");

EP 613 618 ("4-carboxymethyl-chroman-4-carboxylic acid");

U.S. Pat. No. 5,215,570 ("N-(2-methoxy-benzoyl)-4-(3-methylureido)-benzenesulfonamide");

EP 929 543 ("3-oxo-isothiochroman-4-ylidenemethoxy)-acetic acid methyl ester").

The herbicidally active compounds from amongst groups D1 to D16 are described, for example, in "Herbizide [Herbicides]", Hock, Fedtke, Schmidt, 1st edition, Thieme 1995 (s. "quinclorac" p. 238, "molinat" p. 32, "butachlor" p. 32, "pretilachlor" p. 32, "dithiopyr" p. 32, "mefenacet" p. 32, "fenoxapropethyl" p. 216, "dimepiperate" p. 32, "pyrazolynate" p. 146, "pyrazoxyfen" p. 146, "benfuresate" p. 233, "bromobutide" p. 243, "dymron" p. 243, "dimethyametryn" p. 118, "esprocarb" p. 229, "pyributicarb" p. 32, "cinemthylin" p. 32, "propanil" p. 32, "2,4-D" p. 30, "bentazon" p. 30, "mecoprop-P" p. 237, "chlorpropham" p. 205, "ethoxyfen" p. 30, "haloxyfop-P-methyl" p. 38, "haloxyfop-ethoxyethyl" p. 38, "flumicloracpentyl" p. 35, "flupropacil" p. 143, "nipyraclofen" p. 145, "pyrithiobac acid" p. 181);

"Agricultural Chemicals", Book II Herbicides, 1993 (s. "thiobencarb" p. 85, "benzofenap" p. 221, "napropanilid" p. 49, "piperophos" p. 102, "anilofos" p. 241, "etobenzamid (HW-52)" p. 54, "sulcotrione (ICIA-0051)" p. 268, "poast" p. 253, "focus" p. 222, "dimethenamid" p. 48, "sulfosate" p. 236, "2,4-DB" p. 10, "dichlorprop-P" p. 6, "flupoxam" p. 44, "prosulfocarb" p. 84, "quinmerac" p. 233, "metazachlor" p. 64, "flurtamone" p. 265, "bromofenoxim" p. 228, "fomesafen" p. 248, "imazamethabenz-methyl" p. 153, "clodinafop-propargyl" p. 214, "fenoxaprop-P-ethyl" p. 208, "fluazifop-P-butyl" p. 207, "quizalofop-P-ethyl" p. 210, "quizalofop-terfuryl" p. 211, "flumioxazin" p. 43, "flumipropyn" p. 267, "sulfentrazone" p. 261, "thiazopyr" p. 226, "pyrithiobac-sodium" p. 266, "amidosulfuron" p. 151);

"Agricultural Chemicals", Book II Herbicides, 13$^{th}$ Edition (s. "carfenstole" p. 284, "pyribenzoxym" p. 279, "diflufenzopyr" p. 90, "ET-751" p. 278, "carfentrazone-ethyl" p. 267, "fluthiacet-methyl" p. 277, "imazapic" p. 160, "butenachlor" p. 54, "tiocarbazil" p. 84, "fluthiamide" p. 62, "isoxaflutole" p. 283, "butroxydim" p. 259,)

"Short Review of Herbicides & PGRs 1991, Hodogaya Chemicals (s. "furyloxyfen" p. 142, "triazofenamid" p. 268, "thenylchlorid (NSK-850)" p. 52, "cumyluron (JC-940)" p. 90, "pendimethalin (AC-92553)" p. 58, "buthidazole" p. 88, "cyprazole" p. 38, "allidochlor" p. 48, "benzoylprop-ethyl" p. 38, "chlorthiamid" p. 150, "diphenamid" p. 34, "flamprop-methyl" p. 40, "fosamin" p. 232, "isoxaben" p. 42, "monalide" p. 32, "naptalam" p. 36, "pronamid" p. 34, "bialaphos" p. 234, "glufosinate-ammonium" p. 234, "glyphosate" p. 232, "amitrol" p. 254, "clomeprop p. 20, "dichlorprop" p. 6, "fenoprop" p. 8, "fluoroxypyr" p. 156, "MCPA" p. 4, "MCPB" p. 8, "mecoprop" p. 6, "napropamide" p. 16, "triclopyr" p. 154, "chloramben" p. 28, "dicamba" p. 26, "clomazone" p. 268, "diflufenican" p. 42, "fluorochloridone" p. 266, "fluridone" p. 156, "asulam" p. 112, "barban" p. 100, "butylate" p. 106, "carbetamide" p. 36, "chlorobufam" p. 100, "cycloate" p. 108, "desmedipham" p. 104, "di-allate" p. 106, "EPTC" p. 108, "orbencarb" p. 112, "pebulate" p. 106, "phen-isopham" p. 118, "phenmedipham" p. 104, "propham" p. 100, "sulfallate" p. 110, "terbucarb" p. 102, "tri-allate" p. 108, "vernolate" p. 108, "acetochlor" p. 48, "alachlor" p. 46, "diethathyl-ethyl" p. 48, "dimethachlor" p. 50, "metolachlor" p. 46, "propachlor" p. 44, "pyrnachlor" p. 44, "terbuchlor" p. 48, "xylachlor" p. 52, "alloxydim" p. 260, "clethodim" p. 270, "cloproxydim" p. 268, "tralkoxydim" p. 270, "dalapon" p. 212, "ethofumesate" p. 124, "benefin" p. 54, "butralin" p. 58, "dinitramin" p. 56, "ethalfluralin" p. 60, "fluchloralin" p. 54, "isopropalin" p. 58, "nitralin" p. 58, "oryzalin" p. 60, "prodiamine" p. 62, "profluralin" p. 54, "trifluralin" p. 54, "dinoseb" p. 128, "dinoseb-acetate" p. 128, "dinoterb" p. 128, "DNOC" p. 126, "acifluorfen-sodium" p. 142, "aclonifen" p. 146, "bifenox" p. 140, "chlornitrofen" p. 138, "difenoxuron" p. 76, "fluorodifen" p. 138, "fluoroglycofen-ethyl" p. 146, "lactofen" p. 144, "nitrofen" p. 136, "nitrofluorfen" p. 140, "oxyfluorfen" p. 140, "cyperquat-chloride" p. 158, "difenzoquat-methylsulfate" p. 160, "diquat" p. 158, "paraquat-dichloride" p. 158, "benzthiazuron" p. 82, "buturon" p. 66, "chlorbromuron" p. 72, "chloroxuron" p. 76, "chlorotoluron" p. 74, "cycluron" p. 84, "dimefuron" p. 88, "diuron" p. 70, "ethidimuron" p. 86, "fenuron" p. 64, "fluometuron" p. 68, "isoproturon" p. 80, "isouron" p. 88, "karbutilate" p. 76, "linuron" p. 72, "methabenzthiazuron" p. 82, "metoxuron" p. 72, "monolinuron" p. 66, "monuron" p. 64, "neburon" p. 72, "siduron" p. 68, "tebuthiuron" p. 86, "trimeturon" p. 64, "isocarbamid" p. 168, "imazamethapyr" p. 172, "imazapyr" p. 170, "imazaquin" p. 170, "imazethapyr" p. 172, "methazole" p. 162, "oxadiazon" p. 162, "tridiphane" p. 266, "bromoxynil" p. 148, "ioxynil" p. 148, "diclofop-methyl" p. 16, "fenthiapropethyl" p. 20, "fluazifop-butyl" p. 18, "haloxyfop-methyl" p. 18, "isoxapyrifop" p. 22, "propaquizafop" p. 24, "quizalofop-ethyl" p. 20, "chlorfenac" p. 258, "chlorfenprop-methyl" p. 258, "chloridazon" p. 174, "maleic hydrazide" p. 162, "norflurazon" p. 174, "pyridate" p. 176, "clopyralid" p. 154, "picloram" p. 154, "ametryn" p. 198, "atrazine" p. 188, "aziprotryne" p. 206, "cyanazine" p. 192, "cyprazine" p. 192, "desmetryne" p. 200, "dipropetryn" p. 202, "eglinazine-ethyl" p. 208, "hexazinone" p. 208, "procyazine" p. 192, "prometone" p. 196, "prometryn" p. 196, "propazine" p. 188, "secbumeton" p. 196, "simazine" p. 188, "simetryn" p. 196, "terbumeton" p. 204, "terbutryn" p. 198, "terbutylazine" p. 190, "trietazine" p. 188, "ethiozine" p. 210, "metamitron" p. 206, "metribuzin" p. 202, "bromacil" p. 180, "lenacil" p. 180, "terbacil" p. 180, "benazolin" p. 262, "bensulide" p. 228, "benzofluor" p. 266, "butamifos" p. 228, "DCPA" p. 28, "dichlobenil" p. 148, "endothal" p. 264, "mefluidide" p. 306, "perfluidone" p. 260, "terbuchlor" p. 48);

"Global Herbicide Directory" First Edition, 1994 (s. "oxadiargyl" p. 96);

"European Directory of Agrochemical Products" Volume 2—Herbicides" Fourth Edition, (s. "buminafos" p. 255).

"The Pesticide Manual", 12$^{th}$ edition ("cloransulam" p. 196, "diclosulam" p. 283, "florasulam" p. 420, "flumetsulam" p. 438, "metosulam" p. 640).

Moreover, the compound "DEH-112" is disclosed in European Patent Application EP-A 302 203. The compound "tepraloxydim" is described in DE-A 33 36 140; the compound "cinidon-ethyl" in DE-A 36 03 789, "fencarbazone" in EP 507 171, "foramsulfuron" in U.S. Pat. No. 5,922,646, "propoxycarbazone" in EP 507 171 and the compound "fluorbentranil" in EP-A 84 893. Other compounds are known from "Brighton Crop Protection Conference—Weeds—1993" (S. "thidiazimin" p. 29, "AC-322140" p. 41, "KIH-6127" p. 47, "KIH-2023" p. 61, "metobenzuron" p. 67). The compound "carfenstrole (CH-900)" is mentioned in EP-A 332 133 and "penoxsulam" is disclosed in U.S. Pat. No. 5,858,924.

The assignment of the active ingredients to the respective mechanisms of action is based on current knowledge. If several mechanisms of action apply to one active ingredient, this substance was only assigned to one mode of action.

The present invention also extends to herbicidal compositions which comprise a herbicidally active amount of a synergistic herbicidal mixture (comprising a compound of group A), a compound of group B), if desired, a compound of group C) and, if desired, a compound of group D) as described above), at least one liquid and/or solid carrier and, if desired, at least one surfactant.

The herbicidal compositions and synergistic herbicidal mixtures according to the invention can effect very good control of broad-leaved weeds and grass weeds in crops such as maize, cereals, rice and soya without damaging the crop plants, an effect observed especially even at low rates of application.

Taking into consideration the variety of application method in question, the herbicidal compositions and synergistic herbicidal mixtures according to the invention can additionally be employed in a further number of crop plants for eliminating undesirable plants. Examples of suitable crops are the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

Moreover, the herbicidal compositions and synergistic herbicidal mixtures according to the invention may also be employed for controlling harmful plants in modified crops. These modified crops are obtained by genetic engineering methods or by breeding, and—as a rule—they are distinguished by particular, advantageous properties, for example by resistance to certain crop protection agents, resistance to plant diseases or pathogens causing plant diseases such as particular insects or microorganism such as fungi, bacteria or viruses. Other particular properties relate, for example, to the harvested material in terms of quality, storing properties, composition and specific constitutions.

The mixtures according to the invention, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The use forms depend on the intended purposes; in any case, they should guarantee the finest possible distribution of the active ingredients according to the invention.

Suitable inert auxiliaries are mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalene-sulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the synergistic herbicidal mixture or the individual active ingredients with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the mixtures according to the invention in the ready-to-use products can be varied within wide ranges. In general, the formulations comprise from 0.01 to 95% by weight, preferably 0.5 to 90% by weight, of the mixture according to the invention.

The compounds of the groups A) and B), if desired, C) and, if desired D), can be formulated jointly, but also separately, and/or applied to the plants, their environment and/or seeds jointly or separately.

In case a compound of group C) is present in the mixture according to the invention it can be used for penetrating the seed of a crop plant (seed dressing), or be incorporated into the seed furrows prior to sowing. The other compounds of the groups A), B) and, if desired, D) are applied then separately from the compound of group C).

It is preferable to apply the active ingredients simultaneously. However, it is also possible to apply them separately.

Moreover, it may be advantageous to apply the herbicidal compositions and synergistic herbicidal mixtures according to the invention, jointly or separately, with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

The mixtures according to the invention and the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal compositions according to the invention are preferably applied by foliar application. Application may be effected, for example, by usual spraying techniques with water as the carrier, using amounts of spray mixture of approx. 100 to 1000 l/ha. The compositions may also be applied by the so-called "low-volume" and "ultra-low-volume" methods, or in the form of so-called granules.

As a rule, the synergistic herbicidal mixtures comprise the compounds of the groups A) and B) if desired, C), and, if desired, D) in such weight ratios that the synergistic effect takes place.

The ratios of the compounds of the groups A) and B) in the mixture preferably range from 1:0.0002 to 1:50.

The ratios of the compounds of the groups A) and C) in the mixture preferably range from 1:0.0002 to 1:50.

The ratios of the compounds of the groups A) and D) in the mixture preferably range from 1:0.001 to 1:400.

The rate of application of pure synergistic herbicidal mixture, i.e. without formulation auxiliaries, amounts to 0.1 to 5000 g/ha, preferably 1 to 2000 g/ha, in particular 5 to 1000 g/ha, of active substance (a.s.), depending on the intended aim, the season, the target plants and growth stage.

The rate of application of picolinafen is 10 to 500 g/ha, as a rule 30 to 100 g/ha, preferably 25 to 75 g/ha, of active substance (a.s.).

The application of the compound of group B) is 0.1 to 500 g/ha, as a rule 0.5 to 150 g/ha, preferably 1 to 100 g/ha, of active substance (a.s.).

Especially the application rate of bensulfuron methyl is 1 to 400 g/ha, as a rule 10 to 250 g/ha, preferably 30 to 100 g/ha, of active substance (a.s.).

Especially the application rate of chlorimuron ethyl is 0.1 to 250 g/ha, as a rule 1 to 50 g/ha, preferably 5 to 15 g/ha, of active substance (a.s.).

Especially the application rate of chlorsulfuron is 0.1 to 500 g/ha, as a rule 1 to 100 g/ha, preferably 5 to 25 g/ha, of active substance (a.s.).

Especially the application rate of cinosulfuron is 10 to 300 g/ha, as a rule 50 to 150 g/ha, preferably 20 to 80 g/ha, of active substance (a.s.).

Especially the application rate of cyclosulfamuron is 5 to 500 g/ha, as a rule 10 to 200 g/ha, preferably 25 to 60 g/ha, of active substance (a.s.).

Especially the application rate of ethametsulfuron methyl is 0.1 to 250 g/ha, as a rule 1 to 100 g/ha, preferably 10 to 20 g/ha, of active substance (a.s.).

Especially the application rate of ethoxysulfuron is 0.1 to 500 g/ha, as a rule 1 to 250 g/ha, preferably 10 to 120 g/ha, of active substance (a.s.).

Especially the application rate of flazasulfuron is 1 to 500 g/ha, as a rule 10 to 250 g/ha, preferably 25 to 100 g/ha, of active substance (a.s.).

Especially the application rate of iodosulfuron methyl is 0.1 to 100 g/ha, as a rule 1 to 25 g/ha, preferably 3 to 10 g/ha, of active substance (a.s.).

Especially the application rate of mesosulfuron methyl is 0.1 to 250 g/ha, as a rule 1 to 50 g/ha, preferably 5 to 15 g/ha, of active substance (a.s.).

Especially the application rate of metsulfuron methyl is 0.1 to 150 g/ha, as a rule 1 to 50 g/ha, preferably 3 to 10 g/ha, of active substance (a.s.).

Especially the application rate of nicosulfuron is 1 to 500 g/ha, as a rule 5 to 250 g/ha, preferably 20 to 70 g/ha, of active substance (a.s.).

Especially the application rate of primisulfuron methyl is 1 to 500 g/ha, as a rule 5 to 200 g/ha, preferably 20 to 40 g/ha, of active substance (a.s.).

Especially the application rate of prosulfuron is 0.5 to 500 g/ha, as a rule 2 to 200 g/ha, preferably 10 to 40 g/ha, of active substance (a.s.).

Especially the application rate of sulfometuron methyl is 1 to 600 g/ha, as a rule 10 to 300 g/ha, preferably 30 to 100 g/ha, of active substance (a.s.).

Especially the application rate of oxasulfuron is 2 to 600 g/ha, as a rule 10 to 300 g/ha, preferably 50 to 100 g/ha, of active substance (a.s.).

Especially the application rate of triasulfuron is 0.1 to 100 g/ha, as a rule 1 to 30 g/ha, preferably 5 to 10 g/ha, of active substance (a.s.).

Especially the application rate of tribenuron methyl is 0.1 to 250 g/ha, as a rule 1 to 100 g/ha, preferably 5 to 30 g/ha, of active substance (a.s.).

Especially the application rate of triflusulfuron methyl is 0.1 to 250 g/ha, as a rule 1 to 100 g/ha, preferably 10 to 20 g/ha, of active substance (a.s.).

Especially the application rate of trifloxysulfuron is 0.1 to 250 g/ha, as a rule 1 to 100 g/ha, preferably 5 to 20 g/ha, of active substance (a.s.).

Especially the application rate of tritosulfuron is 1 to 250 g/ha, as a rule 10 to 100 g/ha, preferably 30 to 50 g/ha, of active substance (a.s.).

Especially the application rate of flupyrsulfuron methyl is 0.1 to 250 g/ha, as a rule 1 to 100 g/ha, preferably 5 to 10 g/ha, of active substance (a.s.).

Especially the application rate of rimsulfuron is 0.1 to 250 g/ha, as a rule 1 to 50 g/ha, preferably 10 to 15 g/ha, of active substance (a.s.).

Especially the application rate of thifensulfuron methyl is 0.1 to 500 g/ha, as a rule 1 to 200 g/ha, preferably 5 to 60 g/ha, of active substance (a.s.).

Especially the application rate of azimsulfuron is 0.5 to 250 g/ha, as a rule 5 to 75 g/ha, preferably 15 to 25 g/ha, of active substance (a.s.).

Especially the application rate of halosulfuron methyl is 1 to 500 g/ha, as a rule 5 to 200 g/ha, preferably 20 to 90 g/ha, of active substance (a.s.).

Especially the application rate of imazosulfuron is 5 to 500 g/ha, as a rule 25 to 250 g/ha, preferably 75 to 100 g/ha, of active substance (a.s.).

Especially the application rate of sulfosulfuron is 1 to 500 g/ha, as a rule 2 to 250 g/ha, preferably 10 to 50 g/ha, of active substance (a.s.).

Especially the application rate of pyrazosulfuron is 1 to 300 g/ha, as a rule 5 to 100 g/ha, preferably 15 to 30 g/ha, of active substance (a.s.).

The preferred rate of application of the optional compound of group C) is 0.1 to 700 g/ha (a.s.).

As a rule the application rate of dichlormid is 100 to 500 g/ha, of active substance (a.s.).

As a rule the application rate of benoxacor is 20 to 150 g/ha, of active substance (as.).

As a rule the application rate of cloquintocet is 1 to 50 g/ha, of active substance (a.s.).

As a rule the application rate of isoxadifen is 25 to 150 g/ha, of active substance (a.s.).

As a rule the application rate of mefenpyr is 5 to 250 g/ha, of active substance (a.s.).

The preferred rate of application of the optional compound of group D) is 0.5 to 4000 g/ha, of active substance (a.s.).

As a rule the application rate of a sulfonylurea of group D) is from 0.5 to 250 g/ha, as a rule from 1 to 125 g/ha, of active substance (a.s.).

USE EXAMPLES

The mixtures according to the invention were applied pre- or post-emergence (foliar treatment). The herbicidal compounds of groups A) and B) and, if desired, C) and, if desired, D) were applied in the formulation in which they are present as commercially available product.

The herbicidally active compounds of the groups A), B) and, if desired, C) and, if desired, D) were applied in succession or jointly, in the latter case in some cases as a tank mix and in some cases as a readymix, in the form of emulsions, aqueous solutions or suspensions, the vehicle being water (300-400 l/ha). In the case of the field trials, application was effected with the aid of a mobile plot sprayer.

The test period extended over 3 to 8 weeks, and the stands were also observed at later points in time.

Damage by the herbicidal compositions was evaluated with reference to a scale of 0% to 100% in comparison with untreated control plots. 0 means no damage and 100 means complete destruction of the plants.

The following examples will demonstrate the action of the herbicidal compositions which can be used according to the invention, without excluding the possibility of other uses.

In these examples, the value E at which only an additive effect of the individual active ingredients is to be expected was calculated by the method of S. R. Colby (Calculating synergistic and antagonistic responses of herbicide combinations, Weeds 15, 20 pp (1967)).

This was done using the formula $$E = X + Y - \frac{XY}{100}$$

where
X=Percentage of the herbicidal action of the compound of group A) at an application rate of a;
Y=Percentage of the herbicidal action of the compound of group B) at an application rate of b;
E=expected herbicidal action of the compounds of the groups A)+B) at rates of application a+b (in %).

If the value observed exceeds the value E calculated in accordance with Colby's formula, then synergism is present.

The herbicidal mixtures according to the invention, like picolinafen and chlorsulfuron or picolinafen and triasulfuron at appropriate application rates under post emergence conditions, exert a greater herbicidal action than would have been expected according to Colby on the basis of the observed effects of the individual components when used alone.

The invention claimed is:

1. A synergistic herbicidal mixture consisting of the following active ingredients:

A) picolinafen (I)

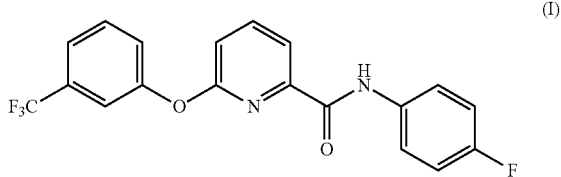 [SMILES: O=C(Nc1ccc(F)cc1)c1cccc(Oc2cccc(C(F)(F)F)c2)n1]

or one of its environmentally compatible salts;
and

B) a synergistically effective amount of a sulfonylurea selected from the group consisting of chlorsulfuron, cinosulfuron, ethametsulfuron, flazasulfuron, flupyrsulfuron, halosulfuron, imazosulfuron, metsulfuron, nicosulfuron, prosulfuron, pyrazosulfuron, rimsulfuron, sulfosulfuron, triasulfuron, tribenuron, triflusulfuron, trifloxysulfuron, tritosulfuron, and an environmentally compatible salt or ester thereof;
and, if desired, C) a safener selected from the group consisting of dichlormid, benoxacor, LAB 145 138, MG-191, furilazole, cyometrinil, oxabetrinil, fluxofenim, flurazole, naphthalic acid anhydride, fenclorim, fenchlorazole-ethyl, mefenpyr, isoxa-difen, cloquintocet, 1-ethyl-4-hydroxy-3(1H-tetrazol-5-yl)-1H-quinolin-2-one, 4-carboxymethyl-chroman-4-carboxylic acid, N-(2-methoxybenzyl)-4-(3-methylureido)-benzenesulfonamide and (3-oxo-isothio-chroman-4-ylidenmethoxy)acetic acid methyl ester;

or one of its environmentally compatible salts, esters or amides.

2. A synergistic herbicidal mixture as claimed in claim 1 wherein component B) is a sulfonylurea selected from the group consisting of chlorsulfuron, ethametsulfuron, flazasulfuron, halosulfuron, imazosulfuron, nicosulfuron, prosulfuron, pyrazosulfuron, rimsulfuron, triasulfuron, triflusulfuron, and an environmentally compatible salt or ester thereof.

3. A synergistic herbicidal mixture as claimed in claim 1 wherein component B) is a sulfonylurea selected from the group consisting of chlorsulfuron, flupyrsulfuron, metsulfuron, prosulfuron, sulfosulfuron, triasulfuron, tribenuron, tritosulfuron, and its environmentally compatible salts or esters.

4. A synergistic herbicidal mixture as claimed in claim 1 wherein component B) is a sulfonylurea selected from the group consisting of chlorsulfuron, flupyrsulfuron, metsulfuron, prosulfuron, sulfosulfuron, triasulfuron, tribenuron, tritosulfuron, and an environmentally compatible salt or ester thereof.

5. A synergistic herbicidal mixture as claimed in claim 1 comprising, as component B) at least a sulfonylurea selected from the group of chlorsulfuron, prosulfuron or triasulfuron, or an environmentally compatible salt or ester thereof.

6. A synergistic herbicidal mixture as claimed in claim 1 wherein component C) is selected from the group consisting of cloquintocet, isoxadifen and mefenpyr.

7. A synergistic herbicidal mixture as claimed in claim 1 wherein the ratios of the compounds of the groups A) and C) range from 1:0.0002 to 1:50.

8. A herbicidal composition comprising the herbicidally active amount of a synergistic herbicidal mixture as claimed in claim 1, at least one liquid and/or solid carrier and, if desired, at least one surfactant.

9. A process for the preparation of the herbicidal composition as claimed in claim 7, comprising mixing the compounds of group A), B), if desired, C), at least one liquid and/or solid carrier and, if desired, at least one surfactant.

10. A method for controlling undesired vegetation, which comprises applying to undesired plants the synergistic herbicidal mixture as claimed in claim 1, during and/or after the emergence of undesired plants, it being possible for the active compounds of the groups A), B), if desired, C) and, if desired D) to be applied simultaneously or in succession.

11. A method for controlling undesired vegetation comprising simultaneously or successively applying to undesired plants, their habitation or their seeds, an herbicidal mixture comprising active ingredients consisting of A) picolinafen (I)

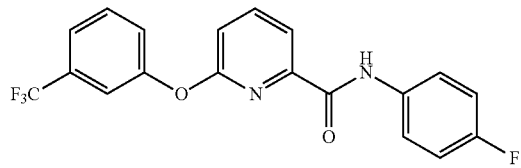

(I)

or one of its environmentally compatible salts;
and

B) a synergistically effective amount of at least one sulfonylurea selected from the group consisting of chlorsulfuron, cinosulfuron, ethametsulfuron, flazasulfuron, flupyrsulfuron, halosulfuron, imazosulfuron, metsulfuron, nicosulfuron, prosulfuron, pyrazosulfuron, rimsulfuron, sulfosulfuron, triasulfuron, tribenuron, triflusulfuron, trifloxysulfuron, tritosulfuron, and an environmentally compatible salt or ester thereof;
and, if desired, C) one safener selected from the group consisting of dichlormid, benoxacor, LAB 145 138, MG-191, furilazole, cyometrinil, oxabetrinil, fluxofenim, flurazole, naphthalic acid anhydride, fenclorim, fenchlorazole-ethyl, mefenpyr, isoxa-difen, cloquintocet, 1-ethyl-4-hydroxy-3(1H-tetrazol-5-yl)-1H-quinolin-2-one, 4-carboxymethyl-chroman-4-carboxylic acid, N-(2-methoxybenzyl)-4-(3-methylureido)-benzenesulfonamide and (3-oxo-isothio-chroman-4-ylidenmethoxy)acetic acid methyl ester;

or one of its environmentally compatible salts, esters or amides.

* * * * *